US012672817B2

(12) United States Patent　　　　　(10) Patent No.:　　US 12,672,817 B2
Chance et al.　　　　　　　　　　　　(45) Date of Patent:　　　　Jul. 7, 2026

（54）　BRAIN IMAGING

（71）　Applicant: Oxford University Innovation Limited, Oxford (GB)

（72）　Inventors: Steven Chance, Oxford (GB); Mark Jenkinson, Oxford (GB); Mario Torso, Oxford (GB)

（73）　Assignee: Oxford University Innovation Limited, Oxford (GB)

（ * ）　Notice:　Subject to any disclaimer, the term of this patent is extended or adjusted under 35 U.S.C. 154(b) by 925 days.

（21）　Appl. No.:　17/296,362

（22）　PCT Filed:　Dec. 9, 2019

（86）　PCT No.:　PCT/GB2019/053473

§ 371 (c)(1),
　　　　(2) Date:　May 24, 2021

（87）　PCT Pub. No.: WO2020/120941

PCT Pub. Date: Jun. 18, 2020

（65）　　　　Prior Publication Data

US 2022/0022804 A1　　　Jan. 27, 2022

（30）　　　Foreign Application Priority Data

Dec. 10, 2018　(GB) ...................................... 1820053
　　Jun. 26, 2019　(GB) ...................................... 1909180
　　Jul. 10, 2019　(GB) ...................................... 1909907

（51）　Int. Cl.
　　　　*A61B 5/00*　　　　(2006.01)
　　　　*A61B 5/055*　　　(2006.01)
　　　　*G01R 33/563*　　(2006.01)
（52）　U.S. Cl.
　　　　CPC .......... *A61B 5/4088* (2013.01); *A61B 5/0042* (2013.01); *A61B 5/055* (2013.01); *G01R 33/56341* (2013.01)

（58）　Field of Classification Search
　　　　CPC ..... A61B 5/4088; A61B 5/0042; A61B 5/055; G01R 33/56341
　　　　See application file for complete search history.

（56）　　　　　References Cited

U.S. PATENT DOCUMENTS 10,573,414 B2　　2/2020　Kamali-Zare et al.
　　2005/0007100 A1*　1/2005　Basser ............. G01R 33/56341
　　　　　　　　　　　　　　　　　　　　　　324/300

(Continued)

FOREIGN PATENT DOCUMENTS

CN　　104207776 A1　12/2014
　　EP　　2 141 506 A2　　1/2010
　　　　　　　　(Continued)

OTHER PUBLICATIONS

International Search Report and Written Opinion for WO 2020/120941 (PCT/GB2019/053473), dated Feb. 28, 2020, pp. 1-20.
　　　　　　　　(Continued)

*Primary Examiner* — Sean A Frith
(74) *Attorney, Agent, or Firm* — Meunier Carlin & Curfman LLC

（57）　　　　ABSTRACT

The present disclosure relates generally to medical imaging and, more particularly, it relates to methods and systems for performing processing of magnetic resonance (MR) imaging of the brain which may be useful in the diagnosis of cognitive disorders. More specifically, the invention includes methods for processing cortical diffusion data from a region of a subject's brain, comprising determining values for the Axial Columnar Refraction (ACR) using values for AngleR and Axial Diffusivity.

11 Claims, 9 Drawing Sheets

Voxel boundary

(56) References Cited

U.S. PATENT DOCUMENTS

| | | | | |
|---|---|---|---|---|
| 2005/0283054 | A1 | 12/2005 | Reiman | |
| 2006/0261808 | A1* | 11/2006 | Huang | G01R 33/56341 |
| | | | | 324/307 |
| 2011/0282183 | A1 | 11/2011 | Song et al. | |
| 2016/0018504 | A1 | 1/2016 | Magin et al. | |
| 2017/0261584 | A1* | 9/2017 | James | G01R 33/4833 |
| 2018/0049665 | A1* | 2/2018 | Jeong | A61B 5/055 |
| 2018/0143282 | A1 | 5/2018 | Chance et al. | |

FOREIGN PATENT DOCUMENTS

| | | | | |
|---|---|---|---|---|
| WO | WO-2013040086 | A1 * | 3/2013 | A61B 5/0042 |
| WO | WO-2016162682 | A1 * | 10/2016 | A61B 5/055 |

OTHER PUBLICATIONS

UK Search Report for GB 1820053.5, dated Jun. 7, 2019, pp. 1-4.
Smith S M et al: "Tract-based spatial statistics: Voxelwise analysis of multi-subject diffusion data", Neuroimage, Elsevier, Amsterdam, NL, vol. 31, No. 4, Jul. 15, 2006 (Jul. 15, 2006), pp. 1487-1505.
Meijer Frederick J et al: "Conventional 3T brain MRI and diffusion tensor imaging in the diagnostic workup of early stage parkinsonism", Neuroradiology, Springer, DE, vol. 57, No. 7, Apr. 7, 2015 (Apr. 7, 2015), pp. 655-669.
Lee Wook et al: "SVM-Based Classification of Diffusion Tensor Imaging Data for Diagnosing Alzheimer's Disease and Mild Cognitive Impairment", Aug. 11, 2015 (Aug. 11, 2015), International Conference on Financial Cryptography and Data Security; [Lecture Notes in Computer Science; Lect.Notes Computer], Springer, Berlin, Heidelberg, pp. 489-499.
First Office Action in connection to CN Application No. 201980081106. X, dated Dec. 8, 2023.
Decision of Refusal relating to Japanese Application No. 2021-554789, dated Mar. 26, 2024.
Andersson JLR, Graham MS, Zsoldos E, Sotiropoulos SN. (2016). Incorporating outlier detection and replacement into a non-parametric framework for movement and distortion correction of diffusion MR images. Neuroimage, 141, 556-572.
Anwander, A., Pampel, A., & Knosche, T. R. (2010). In vivo measurement of cortical anisotropy by diffusion-weighted imaging correlates with cortex type. In Proc. Int. Soc. Magn. Reson. Med (vol. 18, p. 109)—Summary Provided.
Anwander, A., Pampel, A., & Knösche, T. R. (2010). In vivo measurement of cortical anisotropy by diffusion-weighted imaging correlates with cortex type. Talk presented at ISMRM Joint Annual Meeting. Stockholm, Sweden. May 1, 2010-May 7, 2010 https:// pure.mpg.de/pubman/faces/ViewItemOverviewPage.jsp?itemId= item_723666_3.
Barazany, D., & Assaf, Y. (2011). Visualization of cortical lamination patterns with magnetic resonance imaging. Cerebral Cortex, 22(9), 2016-2023.
Beaulieu, C. (2002). The basis of anisotropic water diffusion in the nervous system—a technical review. NMR in Biomedicine, 15(7-8), 435-455.
Benjamini, Y., & Yekutieli, D. (2001). The control of the false discovery rate in multiple testing under dependency. Annals of statistics, 1165-1188.
Braak H, Braak E. Neuropathological staging of Alzheimer-related changes. Acta Neuropathol. 82:239-259 (1991).
Buxhoeveden DP, Switala AE, Litaker M, Roy E, Casanova MF. Lateralization of minicolumns in human planum temporale isabsent in nonhuman primate cortex. Brain Behav Evol 2001; 57:349-58.
Buxhoeveden, D. P., & Casanova, M. F. (2002). The minicolumn hypothesis in neuroscience. Brain, 125(5), 935-951.
Casanova MF, Switala AE. Minicolumnar Morphometry: Computerized Image Analysis. In: Casanova MF, editor.Neocortical Modularity and the Cell Minicolumn. New York:Nova Biomedical; 2005. p. 161-80.

Casanova, M. F., Buxhoeveden, D. P., Switala, A. E., & Roy, E.(2002). Minicolumnar pathology in autism. Neurology, 58(3), 428-432.
Casanova, M. F., Konkachbaev, A. I., Switala, A. E., & Elmaghraby, A. S (2008). Recursive trace line method for detecting myelinated bundles: a comparison study with pyramidal cell arrays. Journal of neuroscience methods, 168(2), 367-372.
Chance S.A. et al. Micro-anatomical correlates of cognitive ability and decline: normal ageing, MCI and Alzheimer's disease, Cerebral Cortex 21(8):1870-8 (2011).
Chance S.A.; Casanova M.F.; Switala A.E.; Crow T.J.; Esiri M.M. Minicolumn thinning in temporal lobe association cortex but not primary auditory cortex in normal human ageing. Acta Neuropathologica 111(5):459-64 (2006).
Chance, S. A., Casanova, M. F., Switala, A. E., & Crow, T. J. (2008). Auditory cortex asymmetry altered minicolumn spacing and absence of ageing effects in schizophrenia. Brain, 131(12), 3178-3192.
Chance, S. A., Sawyer, E. K., Clover, L. M., Wicinski, B., Hof, P. R., & Crow, T. J. (2013). Hemispheric asymmetry in the fusiform gyrus distinguishes *Homo sapiens* from chimpanzees. Brain Structure and Function, 218(6), 1391-1405.
Chance, SA; Tzotzoli, PM; Vitelli, A; Esiri, MM; Crow, TJ. The cytoarchitecture of sulcal folding in Heschl's sulcus and the temporal cortex in the normal brain and schizophrenia: lamina thickness and cell density. Neuroscience Letters 367 (3): 384-388 (2004).
Cohen-Adad, J., Polimeni, J. R., Helmer, K. G., Benner, T., McNab, J. A., Wald, L. L., . . . & Mainero, C. (2012). T2* mapping and B0 orientation-dependence at 7 T reveal cyto-and myeloarchitecture organization of the human cortex. Neuroimage, 60(2), 1006-1014.
D'arceuil, H., & de Crespigny, A. (2007). The effects of brain tissue decomposition on diffusion tensor imaging and tractography. Neuroimage, 36(1), 64-68.
Di Rosa E, Crow TJ, Walker MA, Black G, Chance SA (2009) Reduced neuron density, enlarged minicolumn spacing and altered ageing effects in fusiform cortex in schizophrenia. Psychiatry Res 166:102-115.
Dumoulin, S. O., Fracasso, A., van der Zwaag, W., Siero, J. C., & Petridou, N. (2018). Ultra-high field MRI: advancing systems neuroscience towards mesoscopic human brain function. Neuroimage, 168, 345-357.
Esiri, M. M.; Chance, S. A. Vulnerability to Alzheimer's pathology in neocortex: The roles of plasticity and columnar organization. Journal of Alzheimer's Disease 9(Suppl 3): 79-89 (2006).
Fatterpekar, G. M., Naidich, T. P., Delman, B. N., Aguinaldo, J. G., Gultekin, S. H., Sherwood, C. C., . . . & Fayad, Z. A. (2002). Cytoarchitecture of the human cerebral cortex: MR microscopy of excised specimens at 9.4 Tesla. American journal of neuroradiology, 23(8), 1313-1321.
Fisher, E., Rudick, R. A., Simon, J. H., Cutter, G., Baier, M., Lee, J. C., . . . & Simonian, N. A. (2002). Eight-year follow-up study of brain atrophy in patients with MS. Neurology, 59(9), 1412-1420.
Harasty, J., Seldon, H. L., Chan, P., Halliday, G., & Harding, A. (2003). The left human speech-processing cortex is thinner but longer than the right. Laterality: Asymmetries of Body, Brain and Cognition, 8(3), 247-260.
Hasan, K. M., Sankar, A., Halphen, C., Kramer, L. A., Brandt, M. E., Juranek, J., . . . & Ewing-Cobbs, L. (2007). Development and organization of the human brain tissue compartments across the lifespan using diffusion tensor imaging. Neuroreport, 18(16), 1735-1739.
Heidemann, R. M., Anwander, A., Feiweier, T., Eichner, C., Lützkendorf, R., Bernarding, J., . . . & Turner, R. (2012). Sub-millimeter diffusion MRI at 7T: Does resolution matter?
Heidemann, R. M., Anwander, A., Knösche, T. R., Feiweier, T., Fasano, F., Pfeuffer, J., & Turner, R. (2009). High Resolution Diffusion-Weighted Imaging Showing Radial Anisotropy in the Human Cortex In Vivo. In ISMRM Annual Meeting.
Huang, H., Jeon, T., Sedmak, G., Pletikos, M., Vasung, L., Xu, X., . . . & Mori, S. (2012). Coupling diffusion imaging with histological and gene expression analysis to examine the dynamics of cortical areas across the fetal period of human brain development. Cerebral cortex, 23(11), 2620-2631.

(56) References Cited

OTHER PUBLICATIONS

Ioan Opris Manuel F. Casanova. Prefrontal cortical minicolumn: from executive control to disrupted cognitive processing. Brain, vol. 137, Issue 7, Jul. 1, 2014, pp. 1863-1875 (2014).

Jeon, T., Mishra, V., Uh, J., Weiner, M., Hatanpaa, K. J., White III, C. L., . . . & Huang, H. (2012). Regional changes of cortical mean diffusivities with aging after correction of partial volume effects. Neuroimage, 62(3), 1705-1716.

Jespersen, S. N., Leigland, L. A., Cornea, A., & Kroenke, C. D. (2012). Determination of axonal and dendritic orientation distributions within the developing cerebral cortex by diffusion tensor imaging. IEEE transactions on medical imaging, 31(1), 16-32.

Jones, S. E., Buchbinder, B. R., & Aharon, I.(2000). Three-dimensional mapping of cortical thickness using Laplace's Equation. Human brain mapping, 11(1), 12-32.

Kang, X., Herron, T. J., Turken, U., & Woods, D. L. (2012). Diffusion properties of cortical and pericortical tissue: regional variations, reliability and methodological issues. Magnetic Resonance Imaging, 30(8), 1111-1122.

Kim, T. H., Zollinger, L., Shi, X. F., Rose, J., & Jeong, E. K. (2009). Diffusion tensor imaging of ex vivo cervical spinal cord specimens: the immediate and long-term effects of fixation on diffusivity. The Anatomical Record: Advances in Integrative Anatomy and Evolutionary Biology: Advances in Integrative Anatomy and Evolutionary Biology, 292(2), 234-241.

Kleinnijenhuis, M., Zerbi, V., Küsters, B., Slump, C. H., Barth, M., & van Walsum, A. M. V. C. (2013). Layer-specific diffusion weighted imaging in human primary visual cortex in vitro. Cortex, 49(9), 2569-2582.

Kolasinski, J., Stagg, C. J., Chance, S. A., DeLuca, G. C., Esiri, M. M., Chang, E. H., . . . & Johansen-Berg, H. (2012). A combined post-mortem magnetic resonance imaging and quantitative histological study of multiple sclerosis pathology. Brain, 135(10), 2938-2951.

Kutzelnigg, A., & Lassmann, H. (2006). Cortical demyelination in multiple sclerosis: a substrate for cognitive deficits? Journal of the neurological sciences, 245(1-2), 123-126.

Leuze, C. W., Anwander, A., Bazin, P. L., Dhital, B., Stüber, C., Reimann, K., . . . & Turner, R. (2012). Layer-specific intracortical connectivity revealed with diffusion MRI. Cerebral cortex, 24(2), 328-339.

Leuze, C. W., Dhital, B., Anwander, A., Pampel, A., Heidemann, R., Geyer, S., . . . & Turner, R. (2011). Visualization of the orientational structure of the human stria of Gennari with high-resolution DWI. In Proc Intl Soc Mag Reson Med (vol. 19, p. 2371).

McNab, J. A., Jbabdi, S., Deoni, S. C., Douaud, G., Behrens, T. E., & Miller, K. L. (2009). High resolution diffusion-weighted imaging in fixed human brain using diffusion-weighted steady state free precession. Neuroimage, 46(3), 775-785.

McNab, J. A., Polimeni, J. R., Wang, R., Augustinack, J. C., Fujimoto, K., Stevens, A., . . . & Wald, L. L. (2013). Surface based analysis of diffusion orientation for identifying architectonic domains in the in vivo human cortex. Neuroimage, 69, 87-100.

Miller, K. L., McNab, J. A., Jbabdi, S., & Douaud, G. (2012). Diffusion tractography of post-mortem human brains: optimization and comparison of spin echo and steady-state free precession techniques. Neuroimage, 59(3), 2284-2297.

Miller, K. L., Stagg, C. J., Douaud, G., Jbabdi, S., Smith, S. M., Behrens, T. E., . . . & Jenkinson, N. (2011). Diffusion imaging of whole, post-mortem human brains on a clinical MRI scanner. Neuroimage, 57(1), 167-181.

Mori, S., & Zhang, J. (2006). Principles of diffusion tensor imaging and its applications to basic neuroscience research. Neuron, 51(5), 527-539.

Mountcastle, V. B. (1997). The columnar organization of the neocortex. Brain: a journal of neurology, 120(4), 701-722.

Osteotronix and Fine Structure Analysis—fineSA®, Extending the limits of MRI available on-line at: http://www.acuitasmedical.com/index.php 7 pages.

Peters, A., Sethares, C., & Killiany, R. J. (2001). Effects of age on the thickness of myelin sheaths in monkey primary visual cortex. Journal of Comparative Neurology, 435(2), 241-248.

Preziosa P., Kiljan S., Steenwijk M.D., Meani A., van de Berg W.D.J., Schenk G.J., Rocca M.A., Filippi M., Geurts J.J.G., Jonkman L.E. (2019) Axonal degeneration as substrate of fractional anisotropy abnormalities in multiple sclerosis cortex. Brain. Jun 5. doi: 10.1093/brain/awz143. [Epub ahead of print] Quester.

Quester R, Schroder R. The shrinkage of the human brain stem during formalin fixation and embedding in paraffin. J Neurosci Methods 75:81-89. (1997).

Sarlls, J. E., & Pierpaoli, C. (2009). In vivo diffusion tensor imaging of the human optic chiasm at sub-millimeter resolution. Neuroimage, 47(4), 1244-1251.

Schmierer, K., Wheeler-Kingshott, C. A., Tozer, D. J., Boulby, P. A., Parkes, H. G., Yousry, T. A., . . . & Miller, D. H. (2008). Quantitative magnetic resonance of postmortem multiple sclerosis brain before and after fixation. Magnetic Resonance in Medicine: An Official Journal of the International Society for Magnetic Resonance in Medicine, 59(2), 268-277.

Seldon, H. L. (1981). Structure of human auditory cortex. II. Axon distributions and morphological correlates of speech perception. Brain Research, 229(2), 295-310.

Setsompop, K., Fan, Q., Stockmann, J., Bilgic, B., Huang, S., Cauley, S. F., . . . & Wald, L. L. (2018). High-resolution in vivo diffusion imaging of the human brain with generalized slice dithered enhanced resolution: Simultaneous multislice (g Slider-SMS). Magnetic resonance in medicine, 79(1), 141-151.

Shepherd TM, Thelwall PE, Stanisz GJ, Blackband SJ. (2009) Aldehyde fixative solutions alter the water relaxation and diffusion properties of nervous tissue. Magn Reson Med. 62(1):26-34. doi: 10.1002/mrm.21977.

Sigalovsky, I. S., Fischl, B., & Melcher, J. R. (2006). Mapping an intrinsic MR property of gray matter in auditory cortex of living humans: a possible marker for primary cortex and hemispheric differences. Neuroimage, 32(4), 1524-1537.

Smith, S. M., Jenkinson, M., Woolrich, M. W., Beckmann, C. F., Behrens, T. E., Johansen-Berg, H., . . . & Niazy, R. K.(2004). Advances in functional and structural MR image analysis and implementation as FSL. Neuroimage, 23, S208-S219.

Song SK, Sun SW, Ramsbottom MJ, Chang C, Russell J, Cross AH. (2002) Dysmyelination revealed through MRI as increased radial (but unchanged axial) diffusion of water. Neuroimage, 17(3):1429-36.

Sotiropoulos S.N., Jbabdi S., Xu J., Andersson J.L., Moeller S., Auerbach E.J., Glasser M.F., Hernandez M., Sapiro G., Jenkinson M., Feinberg D.A., Yacoub E., Lenglet C., Van Essen D.C., Ugurbil K., Behrens T.E.; WU-Minn HCP Consortium. (2013). Advances in diffusion MRI acquisition and processing in the Human Connectome Project. Neuroimage, 80, 125-143.

Tommerdahl, M., Tannan, V., Holden, J. K., & Baranek, G. T. (2008). Absence of stimulus-driven synchronization effects on sensory perception in autism: Evidence for local underconnectivity? Behavioral and Brain Functions, 4(1), 19.

Uğurbil, K., Xu, J., Auerbach, E. J., Moeller, S., Vu, A. T., Duarte-Carvajalino, J. M., . . . & Strupp, J. (2013). Pushing spatial and temporal resolution for functional and diffusion MRI in the Human Connectome Project. Neuroimage, 80, 80-104.

Van Veluw, SJ; Sawyer, EK; Clover, L; Cousijn, H; De Jager, C; Esiri, MM Esiri; Chance, SA. Prefrontal cortex cytoarchitecture in normal aging and Alzheimer's disease: a relationship with IQ. Brain Structure & Function 217(4): 797-808 (2012).

Vrenken, H., Pouwels, P. J., Geurts, J. J., Knol, D. L., Polman, C. H., Barkhof, F., & Castelijns, J. A. (2006). Altered diffusion tensor in multiple sclerosis normal-appearing brain tissue: cortical diffusion changes seem related to clinical deterioration. Journal of Magnetic Resonance Imaging: An Official Journal of the International Society for Magnetic Resonance in Medicine, 23(5), 628-636.

Wegner, C., Esiri, M. M., Chance, S. A., Palace, J., & Matthews, P. M (2006). Neocortical neuronal, synaptic, and glial loss in multiple sclerosis. Neurology, 67(6), 960-967.

(56)          References Cited

OTHER PUBLICATIONS

Weiner, M. W., Veitch, D. P., Aisen, P. S., Beckett, L. A., Cairns, N. J., Green, R. C. Alzheimer's Disease Neuroimaging Initiative. (2013). The Alzheimer's Disease Neuroimaging Initiative: A review of papers published since its inception Alzheimer's & Dementia: The Journal of the Alzheimer's Association, 9(5), e111-e194.

Woolrich, M. W., Jbabdi, S., Patenaude, B., Chappell, M., Makni, S., Behrens, T., . . . & Smith, S. M. (2009). Bayesian analysis of neuroimaging data in FSL. Neuroimage, 45(1), S173-S186.

Third Office Action for Chinese Application No. 201980081106.X dated Nov. 4, 2024.

Notice of Reasons for Refusal for Japanese Patent Application No. 2024-117355 dated Aug. 26, 2025.

* cited by examiner

Voxel boundary

BRAIN IMAGING

CROSS-REFERENCE TO RELATED APPLICATIONS

This application is the National Stage of International Application No. PCT/GB2019/053473, filed Dec. 9, 2019, which claims priority to GB 1820053.5, filed Dec. 10, 2018, GB 1909180.0, filed Jun. 26, 2019, and GB 1909907.6, filed Jul. 10, 2019, which are entirely incorporated herein by reference.

The present disclosure relates generally to medical imaging and, more particularly, it relates to methods and systems for performing processing of magnetic resonance (MR) imaging of the brain which may be useful in the diagnosis of cognitive disorders.

Diagnosis and treatment of dementia is an increasing problem, given the ageing population. Currently dementia affects over 830,000 people in the UK. However, given the difficulties in accurate diagnosis of these disorders, the actual proportion of people affected by these disorders may be much greater. There are many recognised forms of dementia. These include Alzheimer's disease (AD), cerebrovascular disease (CVD), frontotemporal dementia (FTD), dementia with Lewy Bodies (DLB). Mild Cognitive Impairment (MCI) is considered to be a precursor to dementia.

Current methods of diagnosis usually depend on clinical screening tools in the form of cognitive tests and assessment of behavioural symptoms. Currently, a standard structural brain MRI may often be requested in order to seek evidence of a qualitative (i.e. visually apparent) reduction in hippocampal volume, enlargement of ventricles and the appearance of enlarged sulcal folding of the cerebral cortex. This assessment is subjective and non-specific, and therefore provides additional evidence, but it is not diagnostic in itself. Differential diagnosis of AD from CVD is usually dependent on the clinical assessment of disease course, with progressive cognitive decline being gradual in the case of AD in contrast to 'stepwise' (rapid drops interrupted by 'plateaus' of relative stability). Clearly this is also subjective and open to interpretation.

Current cognitive tests are usually the MMSE (mini-mental state exam) for which 'healthy' is often considered to be a score >24, MCI 21-24 and dementia 20 or less. However, these boundaries are changeable and also open to interpretation. Some consider a score of <30 to be compatible with MCI. An additional test, the MoCA (Montreal cognitive assessment) has recently been found to be sensitive to CVD-type cognitive changes that may be missed by MMSE. However, it does not provide a differential diagnosis.

Currently, Alzheimer's disease and other forms of dementia can only definitively be diagnosed by post-mortem histology. The exact biochemical processes are not sufficiently understood to offer methods that are an accurate alternative to post-mortem examination. Additionally, most existing measurements of neuropathology in dementia depend on assessment of plaques, tangles or individual cells and synapses, which are at the microscopic level and thus cannot be detected using conventional non-invasive brain imaging.

Early diagnosis of these conditions is particularly important for effective clinical intervention to halt or slow progression of the disease, since the neuropathological changes that occur in dementia are thought to start occurring significantly earlier than the appearance of symptoms.

An additional problem in this field of medicine is that, despite some shared risk factors, the clinical course and potential treatment strategies differ between different types of dementia, for example AD and CVD. Cognitive testing gives an indicator of decline in mental function, but with currently available tools it is difficult to discriminate between different types of dementia. Therefore it is particularly important from a clinical perspective to be able to differentiate between different types of dementia so that the appropriate course of action and treatment can be taken.

Currently biomarker detection depends on:
  i) invasive methods for CSF or blood (which carry risk to patients);
  ii) invasive methods for imaging molecular markers in the brain (which carry risk to patients such that they cannot often be repeated); or
  iii) non-invasive brain imaging methods which are based on statistical number-crunching of population samples using standard volumetric MRI or more recent texture analysis of structural MRI (such as T1 or T2, for example).

There remains a need, however, for more accurate non-invasive methods of assessing the presence and/or severity of cognitive disorders including dementia.

An ideal biological marker would be sensitive to age-associated microstructural changes, and be accessible by non-invasive methods such as neuroimaging. As an alternative to the typical biochemical markers of AD, amyloid and tau, the microanatomical alterations in cortical cytoarchitecture and neuropil are a neglected element for tracking the decline of brain structure in late life (Esiri and Chance, 2006). Recent observations have found that the cellular micro-circuits, called minicolumns, which constitute the fundamental structural motif throughout the cerebral cortex, are altered in a graded manner in healthy ageing, mild cognitive impairment (MCI) and Alzheimer's disease (AD) (Chance et al., 2011). This microscopic erosion of columnar architecture correlates with cognitive decline and with traditional markers of AD pathology, e.g. plaque load (Chance et al., 2006). It is detectable independently of cortical volume and there are indications that regionally-specific changes in minicolumn architecture may be associated with different pathologies (Opris & Casanova, 2014).

These alterations can be quantified non-invasively using data derived from MRI scanning and imaging methods applied to the brains of subjects, using different MRI methods including but not limited to diffusion tensor imaging (DTI), Fine Structure Analysis (fineSA™, see: www.acuitasmedical.com/technology.php) and other MRI acquisition methods. The data derived from these imaging studies can then be compared to the predicted pattern of change determined from patients with confirmed diagnoses of such conditions. This comparison of acquired data from a subject of interest with the modelled data derived from patients with confirmed diagnoses will then aid in the assessment and diagnosis of different types of dementia or other cognitive disorders in living subjects, including early stages of dementia.

It has previously been found that signature patterns of minicolumn changes within certain regions of the brain associated with neuropathological conditions do indeed exist and correlate with cognitive ability and decline; and that diffusion MRI measures, particularly DTI, can be used to assess minicolumn structure in the brain (WO2016/162682).

Although DTI is sensitive to white matter microstructure, there has been only limited application of typical methods for in vivo neuroimaging to the microstructure of the cortical grey matter.

The rationale of the present invention was to use histology and post-mortem MRI to explore a novel, non-invasive neuro-imaging biomarker and its correlation with certain elements of the microstructure of the cerebral cortex, with the intention that such a measure could be used in living subjects to assess the progression of cytoarchitectural changes in late life ageing and dementia.

The present invention provides a novel measurement which may be derived from MRI that is shown herein to be sensitive to ageing and dementia-related changes in cortical microstructure using patients with post-mortem confirmed diagnosis. The invention may be particularly useful in providing a method for diagnosing or staging Alzheimer's disease and other dementias using microstructural brain changes. The invention may also be applied to other cognitive disorders or neurological conditions where there are structural changes in the brain.

In one embodiment, the invention provides a method for processing cortical diffusion data from a region of a subject's brain, the method comprising:

(a) obtaining a value for the angle of deviation (AngleR) between the principal diffusion direction and the columnar direction (ColD) of the minicolumns in a first voxel in a region of grey matter in a subject's brain;

(b) obtaining a value for the Axial Diffusivity in a second voxel which is present in the white matter underlying the region of grey matter; and (c) determining a value for the Axial Columnar Refraction (ACR) for the voxels using values for AngleR and Axial Diffusivity.

Preferably, Step (a) comprises:

(a1) determining the principal diffusion direction in a voxel in a region of grey matter in a subject's brain;

(a2) determining the columnar direction (ColD) of the minicolumns in the voxel; and (a3) obtaining a value for the angle of deviation (AngleR) between the principal diffusion direction and ColD.

In some embodiments, the invention provides a method of obtaining an indication of the level of a cognitive disorder in a subject, the method comprising the steps:

(a) obtaining values of ACR by a method of the invention for a plurality of voxels in a region of a subject's brain, wherein the magnitude of the values of ACR for those voxels provides an indication of the level of a cognitive disorder in that subject.

In other embodiments, the invention provides a method of obtaining an indication of the number of microsegment breaks in a region of a subject's brain, the method comprising the steps:

(a) obtaining values of ACR by a method of the invention for a plurality of voxels in a region of a subject's brain, wherein the magnitude of the values of ACR for those voxels provides an indication of the number of microsegment breaks in that region.

The invention also provides a method of obtaining an indication of the level of a cognitive disorder in a subject, the method comprising the steps:

(a) obtaining, in a plurality of voxels in a region of a subject's brain, values for the angle of deviation (AngleR) between the principal diffusion direction and the average columnar direction (ColD) of the minicolumns, wherein the brain region is cortical area 9 or PHG or the entorhinal cortex, and wherein the magnitude of the values of AngleR from the plurality of voxels provides an indication of the level of a cognitive disorder in that subject.

The invention also provides a method of obtaining an indication of the level of MS (multiple sclerosis) in a subject, the method comprising the steps:

(a) obtaining, in a plurality of voxels in a region of a subject's brain, values for the angle of deviation (AngleR) between the principal diffusion direction and the average columnar direction (ColD) of the minicolumns, preferably wherein the brain region is cortical area 9, area 41, or V1 (primary visual cortex)

wherein the magnitude of the values of AngleR from the plurality of voxels provides an indication of the level of MS in that subject.

The invention also provides a method of obtaining an indication of the number of microsegment breaks in a region of a subject's brain, the method comprising the steps:

(a) obtaining, in a plurality of voxels in a region of a subject's brain, values for the angle of deviation (AngleR) between the principal diffusion direction and the average columnar direction (ColD) of the minicolumns, wherein the magnitude of the values of AngleR from the plurality of voxels provides an indication of the number of microsegment breaks in that region.

Preferably, the brain region is cortical area 9 or PHG or the entorhinal cortex.

Preferably, Step (a) comprises:

(a1) determining the principal diffusion direction in a plurality of voxels in a region of a subject's brain;

(a2) determining the columnar direction (ColD) of the minicolumns in the voxels; and (a3) determining a value for the angle of deviation (AngleR) between the principal diffusion direction and ColD for each voxel.

In another embodiment, the invention provides a method of obtaining an indication of the level of a cognitive disorder in a subject, the method comprising the steps:

(a) obtaining, in a plurality of voxels in a region of a subject's brain, values for the axial diffusivity, wherein the brain region is cortical area 9 or PHG or the entorhinal cortex, wherein the magnitude of the values of axial diffusivity from the plurality of voxels provides an indication of the level of a cognitive disorder in that subject.

In another embodiment, the invention provides a method of obtaining an indication of the number of microsegment breaks in a region of a subject's brain, the method comprising the steps:

(a) obtaining, in a plurality of voxels in a region of a subject's brain, values for the axial diffusivity, wherein the magnitude of the values of axial diffusivity from the plurality of voxels provides an indication of the number of microsegment breaks in that region.

Preferably, the brain region is cortical area 9 or PHG or the entorhinal cortex.

In another embodiment, the invention provides a method for processing cortical diffusion data from a region of a subject's brain, the method comprising:

(a) obtaining a value for the perpendicular diffusivity (Perp) in a first voxel in a region of grey matter in a subject's brain;

(b) obtaining a value for the Axial Diffusivity in a second voxel which is present in the white matter underlying the region of grey matter; and (c) determining a value for the Perpendicular Columnar Refraction (PerpCR) for the voxels using values for Perp and Axial Diffusivity.

Preferably, Step (a) comprises the steps:

(a1) obtaining a measurement for cortical diffusion in the first voxel;

(a2) determining, from the measurement for cortical diffusion obtained in Step (a1), the principal diffusion vector ($D_{PDD}$) in the voxel;

(a3) determining the columnar direction (ColD) of the minicolumns in the voxel; and (a4) determining a value for the perpendicular diffusivity (Perp) for the voxel by projecting $D_{PDD}$ onto the plane which is orthogonal to ColD in that voxel and determining the magnitude of the projection.

In other embodiments, the invention provides a method of obtaining an indication of the level of a cognitive disorder in a subject, the method comprising the steps:

(a) obtaining values of Perpendicular Columnar Refraction (PerpCR) by a method of the invention for a plurality of voxels in a region of a subject's brain, wherein the magnitude of the values of Perpendicular Columnar Refraction (PerpCR) for those voxels provides an indication of the level of a cognitive disorder in that subject.

In other embodiments, the invention provides a method of obtaining an indication of the number of microsegment breaks in a region of a subject's brain, the method comprising the steps:

(a) obtaining values of Perpendicular Columnar Refraction (PerpCR) by a method of the invention for a plurality of voxels in a region of a subject's brain, wherein the magnitude of the values of Perpendicular Columnar Refraction (PerpCR) for those voxels provides an indication of the number of microsegment breaks in that region.

In other embodiments, the invention provides a method of obtaining an indication of the level of a cognitive disorder in a subject, the method comprising the steps:

(a) obtaining, in a plurality of voxels in a region of a subject's brain, a value for the perpendicular diffusivity (Perp), wherein the brain region is cortical area 9 or PHG or the entorhinal cortex, wherein the magnitude of the values of Perp from the plurality of voxels provides an indication of the level of a cognitive disorder in that subject.

In other embodiments, the invention provides a method of obtaining an indication of the number of microsegment breaks in a region of a subject's brain, the method comprising the steps:

(a) obtaining, in a plurality of voxels in a region of a subject's brain, a value for the perpendicular diffusivity (Perp), wherein the magnitude of the values of Perp from the plurality of voxels provides an indication of the number of microsegment breaks in that region.

Preferably, the brain region is cortical area 9 or PHG or the entorhinal cortex.

Preferably, Step (a), for each voxel, comprises the steps:

(a1) obtaining a measurement for cortical diffusion in a voxel in a region of a subject's brain;

(a2) determining, from the measurement for cortical diffusion obtained in Step (a1), the principal diffusion vector ($D_{PDD}$) in the voxel;

(a3) determining the columnar direction (ColD) of the minicolumns in the voxel; and (a4) determining a value for the perpendicular diffusivity (Perp) for the voxel by projecting $D_{PDD}$ onto the plane which is orthogonal to ColD in that voxel and determining the magnitude of the projection.

The methods of the invention are preferably computer-implemented methods. Each of the steps of the methods of the invention may be implemented by a computing device. Preferably, the diffusion data is obtained by use of a medical imaging device including a magnetic resonance (MR) scanner. The invention is an ex vivo method.

In one embodiment, the invention provides a method for processing cortical diffusion data from a region of a subject's brain. The cortical diffusion data may include one more of AngleR, Axial Diffusion, Perp and optionally other parameters. The cortical diffusion data is preferably obtained by a neuro-imaging method. Most preferably, the cortical diffusion data is magnetic resonance (MR) relaxometry data. The diffusion data may be measured directly from an MRI scan of the subject's brain or from MRI data previously-obtained from the subject's brain. In some embodiments, the cortical diffusion data may be a value that is derived from the individual brain MRI measurements using mathematical formulas, algorithms, databases and/or look-up tables. In preferred embodiments, the cortical diffusion data is derived from MRI measurements obtained from the brain or from images of the brain.

In all embodiments of this invention, the values, measurements, etc. which are obtained from the subject's brain may be obtained from subject's brain as part of the methods of the invention, or they may be values, measurements, etc., which have previously been obtained from the subject's brain.

In some preferred embodiments of the invention, the cortical diffusion data is obtained by diffusion MRI. As used herein, the term "diffusion MRI" refers to any magnetic resonance imaging (MRI) method which measures the diffusion process of molecules, preferably water molecules, in biological tissues. Diffusion MRI may also be referred to as diffusion tensor imaging (DTI) or diffusion weighted imaging.

The cortical diffusion data may be combined with T1 or T2 or T2* mapping or the MRI measurement may be a spectroscopic measurement combined with T1, T2, or T2* localised to the brain.

In some embodiments, one or more measurements are obtained using the imaging methods described in WO2013/040086 (the contents of which are hereby incorporated by reference) or Fine Structure Analysis™ (fineSA™; Acuitas Medical) or other MRI acquisition methods.

The measurements of cortical diffusion are made in a least one voxel. A voxel is a unit of volume that defines a 3-dimensional space. In this context, a voxel is preferably a unit in the MRI scan which has an associated value for potentially several different parameters, depending on the scan acquisition (e.g. a voxel may have a grey matter intensity value and a principal diffusion direction associated with it).

The methods of the invention are applied to one or more regions of the subject's brain. In preferred embodiments of the invention, the measurements or values are obtained from one or more different regions of the brain, preferably two or more, three or more, four or more, five or more, six or more, seven or more, or eight or more different regions of the brain, most preferably five or more different regions of the brain. In some embodiments, the region of the subject's brain is the whole brain.

In preferred embodiments of the invention, the measurements or values are obtained from or derived from one or more regions of the cortex of the brain. Preferably, the region of the subject's brain is a region of the cortex comprising grey matter with underlying (subcortical) white matter.

In preferred embodiments, the measurements or values are obtained from one or more specific layers of the cortex, preferably from cortical layer 3, cortical layer 5, or cortical layers 3-6. The upper layers 1 and 2 may also be useful. In more preferred embodiments, the measurements or values are obtained from cortical layers 3-6 since these also contain axon bundles which may be useful for DTI signal analysis.

Preferably, the brain regions are selected from the group consisting of parahippocampal gyrus (PHG), fusiform gyrus (Fusi), dorsolateral prefrontal cortex area 9 (dlPFC), Heschl's gyrus (HG), planum temporale (PT), inferior parietal lobule (IPL), middle temporal gyrus (MTG), primary visual cortex (V1; area 17) and the entorhinal cortex.

In some embodiments of the invention, the brain region is preferably the cortical grey matter. In some preferred embodiments, the brain region is cortical area 9 or PHG or the entorhinal cortex. In other preferred embodiments, the brain region is cortical area 9, area 41 or the primary visual cortex, V1.

In some preferred embodiments, the measurements or values are obtained from or derived from 1, 2, 3, 4, 5, 6, 7 or 8 of the above regions.

In preferred embodiments of the invention where the method is used to distinguish between AD and CVD, the measurements or values are obtained from or derived from one or more regions selected from the group consisting of the parahippocampal gyrus (PHG), fusiform gyrus (Fusi), dorsolateral prefrontal cortex (dlPFC), Heschl's gyrus (HG), planum temporale (PT). In some preferred embodiments of the invention where the method is used to distinguish between AD and CVD, the measurements or values are obtained from all of these regions. Use of parameters obtained from or derived from all five of these regions in the methods of the invention has achieved >90% predictive accuracy for differentiating AD from CVD. Additional regions for measurement include frontal lobe, parietal lobe, temporal lobe and occipital lobe In preferred embodiments of the invention where the method is used to obtain an indication of the presence of Mild Cognitive Impairment (MCI), the measurements or values are obtained from or derived from one or more regions of the cortex of the brain, preferably from one or more regions selected from the group consisting of the parahippocampal gyrus (PHG), fusiform gyrus (Fusi), dorsolateral prefrontal cortex (dlPFC), Heschl's gyrus (HG), planum temporale (PT), inferior parietal lobule (IPL), middle temporal gyrus (MTG) and primary visual cortex (V1;). In some preferred embodiments of the invention where the method is used to obtain an indication of the presence of Mild Cognitive Impairment, the measurements or values are obtained from all of these regions.

In preferred embodiments of the invention where the method is used to differentiate FTD from other dementias, the measurements or values are obtained from or derived from one or more regions of the cortex of the brain, preferably from one or more regions selected from the group consisting of the parahippocampal gyrus (PHG), fusiform gyrus (Fusi), dorsolateral prefrontal cortex (dlPFC), Heschl's gyrus (HG), planum temporale (PT), inferior parietal lobule (IPL), middle temporal gyrus (MTG), caudal middle frontal cortex and V1. In the most preferred embodiments of the invention where the method is used to differentiate FTD from other dementias, the measurements or values are obtained from all of these regions.

The regions of the brain defined herein are preferably as defined on Brodmann's cytoarchitectural organisation of the human cortex (Brodmann, 1909). The equivalents may also be seen in Von Economo and Koskinas (Von Economo C, Koskinas G N (1925) Die Cytoarchitektonik der Hirnrinde des Erwachsenen Menschen. Springer, Berlin (Germany) (Translated by Dr Lee Seldon)).

The methods of the invention may also be used to distinguish other cognitive or neuro-psychiatric disorders, as defined below. When the methods of the invention are used to distinguish the disorders recited below, the brain regions analysed should include one or more, more preferably all, of the corresponding brain regions recited below:

Autism: fusiform cortex, superior temporal sulcus, orbitofrontal cortex, dlPFC, inferior parietal cortex, primary visual cortex, primary auditory cortex Schizophrenia: dlPFC, dorsomedial PFC, cingulate gyrus, superior temporal gyrus, PHG Bipolar disorder: PHG, subgenual PFC, dlPFC, cingulate Epilepsy: entorhinal cortex, PHG Dyslexia: inferior parietal cortex, superior temporal gyrus Down's syndrome: superior temporal gyrus, PHG, dlPFC Parkinson's disease: entorhinal cortex, cingulate gyrus Amyotrophic lateral sclerosis: motor cortex Huntington's disease: motor cortex, cingulate gyrus Multiple sclerosis: motor cortex, cortical regions containing MS lesions identified by MRI scan Prion disease: primary visual cortex, cortical areas showing volumetric shrinkage contrasted with cortical area with no discernible shrinkage Depression: dlPFC, dorsomedial PFC, cingulate gyrus Obsessive-compulsive disorder: cingulate gyrus, dlPFC, dorsomedial PFC ADHD: orbitofrontal cortex, dlPFC, cingulate As used herein, the term "minicolumn" is a vertical column through the cortical layers of the brain. Minicolumns may also be referred to interchangeably as cortical minicolumns, microcolumns or cortical microcolumns. The term "minicolumn" may either be understood to be the combination of the cell-dense core and cell-sparse peripheral neuropil space surrounding it or, in some circumstances, just the cell-dense core (defined by the cell bodies). Typically, it relates to the core and periphery.

A microsegment is a fragment of columnar microstructural organisation arising from a disrupted string of aligned cells, connective dendrites or axons, which is not classified as a minicolumn based on insufficient continuity of structure, reduced number of cells or increased inter-cell distance. Microsegments are described histopathologically in Chance S. A. et al. "Micro-anatomical correlates of cognitive ability and decline: normal ageing, MCI and Alzheimer's disease", Cerebral Cortex 21(8):1870-8 (2011).

The subject may be any animal, preferably a mammal, most preferably a human. In some embodiments, the subject may be one with a cognitive disorder, preferably one with dementia.

In some embodiments, the subject is one which has Alzheimer's Disease (AD), cerebrovascular dementia (CVD), mild cognitive impairment (MCI), frontotemporal dementia (FTD), or dementia with Lewy Bodies (DLB). Preferably, the subject has Alzheimer's disease, FTD, CVD or MCI.

In other embodiments, the subject may be one with a neurological disorder associated with changes in normal brain structure.

In some embodiments, the subject is one which has autism, multiple sclerosis (MS), epilepsy, amyotrophic lateral sclerosis (ALS), Parkinson's disease, schizophrenia, bipolar disorder, dyslexia, Down's syndrome, Huntington's disease, prion disease, depression, obsessive-compulsive disorder or attention deficit hyperactivity disorder (ADHD).

In other embodiments, the subject is one which has a condition selected from the group consisting of Subjective Cognitive Impairment, preMCI, and prodromal AD, Posterior Cortical Atrophy (subset of AD), Behavioural, Semantic, Progressive Non-fluent Aphasia (subsets of FTD), encephalopathy, hepatic encephalopathy, stroke, ischaemia, ischaemic hypoxia, neuro-inflammation, traumatic brain injury (TBI), mild TBI, chronic traumatic encephalopathy, concussion and delirium.

In some embodiments, the subject is older than 1, 5, 10, 20, 30, 40, 50, 60, 70, 80 or 90 years old. In other embodiments, the subject is 5-100, 10-100, 20-100, 30-100, 40-100, 50-100, 60-100, 70-100, 80-100 or 90-100 years old. In other embodiments, the subject is 1-5, 5-10, 10-20, 20-30, 30-40, 40-50, 50-60, 60-70, 70-80, 80-90 or 90-100 years old.

In some embodiments, the subject is not a foetus.

Some embodiments of the invention involve the step of obtaining a measurement for cortical diffusion in a voxel in a region of a subject's brain.

The cortical diffusion data may be obtained de novo, i.e. directly from the subject, or it might have previously been obtained from the subject. In the latter case, the data may be obtained from a graph, look-up table, database or mathematical equation, or the like.

Some embodiments of the invention involve the step of determining the principal diffusion direction or principal diffusion vector ($D_{PDD}$) in the voxel in the region of the subject's brain. In this context, diffusion refers to the diffusion of water through the microscopic structure of the brain tissue (including minicolumns). The principal diffusion vector is a standard measurement in DTI, being the eigenvector corresponding to the largest eigenvalue of the diffusion tensor. The tensor is in essence the covariance matrix of a 3D Gaussian distribution that models the Brownian motion of the water molecules within a voxel. Preferably, the principal diffusion direction or vector ($D_{PDD}$) is obtained from the measurement for cortical diffusion.

Some embodiments of the invention involve the step of determining or estimating the columnar direction (ColD) of the minicolumns in the voxel. As used herein, the terms "ColD" and "CRadial" may be used interchangeably. Furthermore, the terms "radial columnar direction", "radial direction" and "columnar direction" may also be used interchangeably.

This determination or estimation may be based on cortical profiles spanning the cortex. It is a mathematical estimate of the minicolumn direction derived from typical healthy minicolumn structure based on histology. It is estimated for each region and each brain based on anatomical features. ColD may be obtained de novo, i.e. directly from the subject, or it might have previously been obtained from the subject or from other subject. In the latter case, the data may be obtained from a graph, look-up table, database or mathematical equation, or the like. There will be many minicolumns in a typical voxel (e.g. 1 mm³). Therefore, the value of ColD for a voxel will be an average value.

Some embodiments of the invention involve the step of determining the angle of columnar deviation (AngleR) between ColD and the direction of $D_{PDD}$ for the voxel. AngleR is measured on an individual voxel level. AngleR is determined in grey matter voxels. It is measured in radians.

In some embodiments of the invention, a value for Axial Diffusivity is obtained for the second voxel. The second voxel is present in the white matter of the brain.

As used herein, the term "axial diffusivity" refers to the diffusivity along the principal axis of diffusion, $\lambda_1$. Axial diffusivity is also known as longitudinal diffusivity. Axial diffusivity is measured in mm² per second.

The value for Axial Diffusivity is obtained in a second voxel (or second set of voxels) which is present in the white matter underlying the region of grey matter (which comprises the first voxel or first set of voxels).

The voxels in grey matter used to derive AngleR should be approximately overlying a corresponding set of voxels in sub-cortical white matter used to derive Axial Diffusivity. The first and second voxels should be within the same, or a connected, brain region.

The first voxels should form a set of contiguous or semi-contiguous grey matter voxels within a defined cortical region. The second voxels should form a set of contiguous or semi-contiguous white matter voxels within the same overall brain region or a brain region with known connections to the cortical region.

In some embodiments, the first and/or second voxels are ones which form a set of contiguous or semi-contiguous voxels which form a continuous or discontinuous arc across the cortex of the subject's brain.

The second voxel will lie beneath the first voxel in the radial direction. It does not need to be adjacent as the border region may be excluded. The second voxel (or set of voxels) will lie within the white matter of the same brain region as the grey matter containing the first voxel (or set of voxels) based on anatomical knowledge or on an automated assignment to regions using a probabilistic brain atlas, usually based on a prior database.

In some embodiments of the invention include the step of determining a value for the Axial Columnar Refraction (ACR) for the voxel or voxels using values for AngleR and A×D.

Axial Columnar Refraction is a value which is derived from the values for AngleR and Axial Diffusivity. It is a value which is representative of, and directly (preferably positively) correlated with, the number and density of microsegments, and the degree of abnormal cortical minicolumn structure in a subject's brain, and hence the degree of cognitive decline in a subject.

In some embodiments, ACR is the sum or weighted sum of AngleR and Axial Diffusivity, i.e. (k1×AngleR)+(k2× Axial Diffusivity), where k1 and k2 are independently positive numbers which may be the same or different. Most preferably, ACR is the product of AngleR and Axial Diffusivity (i.e. AngleR×Axial Diffusivity) or a multiple thereof. ACR may be assigned to the first and/or second voxel.

In some embodiments, a grey matter voxel may be "matched" (i.e. combined) with more than one white matter voxel (or vice versa). In this case, an average would be calculated.

In some embodiments, the method comprises obtaining or determining values for both AngleR and Axial Diffusivity in a plurality of voxels. For example, values for AngleR and Axial Diffusivity may independently be obtained or determined in 1-10,000, preferably 50-6,000, more preferably 100-500 voxels. For a whole-brain analysis, values for AngleR may be obtained from 140,000-180,000, preferably about 160,000, grey matter voxels and combined with values for Axial Diffusivity for an equal number of white matter voxels.

Optionally, the average value for the Axial Columnar Refraction (ACR) for the selected voxels is determined using the average values for AngleR and Axial Diffusivity in each of those voxels. Alternatively, some other mathematical function of AngleR and Axial Diffusivity may be selected (e.g. weighted sum of AngleR and Axial Diffusivity) to provide a value for ACR.

In some embodiments, the invention provides a method of obtaining an indication of the level of a cognitive disorder in a subject, the method comprising the steps:

(a) obtaining values of ACR by a method of the invention for a plurality of voxels in a region of a subject's brain, wherein the magnitude of the values of ACR for those voxels provides an indication of the level of a cognitive disorder in that subject.

The value of ACR may also be used to distinguish between healthy controls and subjects with cognitive decline, e.g. those with Alzheimer's Disease.

As used herein, the term "cognitive disorder" refers to any mental health disorder that affects learning, memory, perception and/or problem solving. In preferred embodiments of the invention, the cognitive disorder may be any form of dementia.

Preferably, the cognitive disorder is selected from the group consisting of Alzheimer's Disease (AD), cerebrovascular dementia (CVD), mild cognitive impairment (MCI), frontotemporal dementia (FTD) and dementia with Lewy Bodies (DLB).

In other embodiments, the cognitive disorder may be a neurological disorder associated with changes in normal brain structure, preferably a neurological disorder selected from the group consisting of autism, multiple sclerosis (MS), epilepsy, amyotrophic lateral sclerosis (ALS and Parkinson's disease.

In other embodiments, the cognitive disorder is preferably a neuro-psychiatric disorder, most preferably selected from the group consisting of autism, schizophrenia, bipolar disorder, epilepsy, dyslexia, Down's syndrome, Parkinson's disease, amyotrophic lateral sclerosis, Huntington's disease, multiple sclerosis, prion disease, depression, obsessive-compulsive disorder and attention deficit hyperactivity disorder (ADHD).

In other embodiments, the cognitive disorder is Subjective Cognitive Impairment, preMCI, and prodromal AD; Posterior Cortical Atrophy (subset of AD); Behavioural, Semantic, Progressive Non-fluent Aphasia (subsets of FTD); Encephalopathy, Hepatic encephalopathy; Stroke; Ischaemia, Ischaemic hypoxia; Neuro-inflammation; Traumatic brain injury (TBI), mild TBI, chronic traumatic encephalopathy, concussion; and delirium.

The level of dementia may be quantified using the Braak stage (e.g. Braak H, Braak E. 1991. Neuropathological staging of Alzheimer-related changes. Acta Neuropathol. 82:239-259).

In other embodiments, the invention provides a method of obtaining an indication of the number of microsegment breaks in a region of a subject's brain, the method comprising the steps:

(a) obtaining values of ACR by a method of the invention for a plurality of voxels in a region of a subject's brain, wherein the magnitude of the values of ACR for those voxels provides an indication of the number of microsegment breaks in that region.

It is shown herein that ACR is positively correlated with the number of microsegment breaks in that brain region. The number of microsegment breaks in a defined brain region will give an indication of the density of microsegment breaks in that region.

In yet a further embodiment, the invention provides a method of obtaining an indication of the level of a cognitive disorder in a subject, the method comprising the steps:

(a) obtaining, in a plurality of voxels in a region of a subject's brain, a value for the angle of deviation (AngleR) between the principal diffusion direction and the average columnar direction (ColD) of the minicolumns, wherein the brain region is cortical area 9 or PHG or entorhinal cortex, wherein the magnitude of the values of AngleR from the plurality of voxels provides an indication of the level of a cognitive disorder in that subject.

It is shown herein that AngleR is positively correlated with the number of microsegment breaks in that brain region and that this is representative of the level of cognitive disorder.

In yet a further embodiment, the invention provides a method of obtaining an indication of the number of microsegment breaks in a region of a subject's brain, the method comprising the steps:

(a) obtaining, in a plurality of voxels in a region of a subject's brain, a value for the angle of deviation (AngleR) between the principal diffusion direction and the average columnar direction (ColD) of the minicolumns, wherein the magnitude of the values of AngleR from the plurality of voxels provides an indication of the number of microsegment breaks in that region.

Preferably, the brain region is cortical area 9 or PHG or entorhinal cortex. It is shown herein that AngleR is positively correlated with the number of microsegment breaks in cortical area 9 and PHG.

In yet another embodiment, the invention provides a method of obtaining an indication of the level of a cognitive disorder in a subject, the method comprising the steps:

(a) obtaining, in a plurality of voxels in a region of a subject's brain, a value for the axial diffusivity, wherein the brain region is cortical area 9 or PHG or entorhinal cortex, wherein the magnitude of the values of axial diffusivity from the plurality of voxels provides an indication of the level of a cognitive disorder in that subject.

It is shown herein that axial diffusivity is positively correlated with the number of microsegment breaks in cortical area 9 or PHG and that this is representative of the level of cognitive disorder.

In yet another embodiment, the invention provides a method of obtaining an indication of the number of microsegment breaks in a region of a subject's brain, the method comprising the steps:

(a) obtaining, in a plurality of voxels in a region of a subject's brain, a value for the axial diffusivity, wherein the magnitude of the values of axial diffusivity from the plurality of voxels provides an indication of the number of microsegment breaks in that region.

It is shown herein that Axial Diffusivity is positively correlated with the number of microsegment breaks. Preferably, the brain region is cortical area 9 or PHG or entorhinal cortex.

Some embodiments of the invention include the step of determining a value for the Perpendicular Columnar Refraction (PerpCR) for the voxel using values for Axial Diffusivity and Perp. Perpendicular Columnar Refraction (PerpCR) is a value which is derived from the values for Axial Diffusivity and Perp. It is a value which is representative of, and positively correlated with, the number and density of microsegments, and the degree of abnormal cortical minicolumn structure in a subject's brain, and hence the degree of cognitive decline in a subject.

Axial Diffusivity is measured on an individual voxel level. Axial Diffusivity is determined in white matter voxels. It is measured in $mm^2$ per second.

Perp is measured on an individual voxel level. Perp is determined in grey matter voxels. It is measured in $mm^2$ per second. In some embodiments, Perpendicular Columnar Refraction (PerpCR) is the sum or weighted sum of Axial Diffusivity and Perp, i.e. (k1×Axial Diffusivity)+(k2×Perp) where K1 and K2 are independently positive numbers which may be the same or different. Most preferably, Perpendicular Columnar Refraction (PerpCR) is the product of Axial Diffusivity and Perp (i.e. Axial Diffusivity×Perp) or a multiple thereof. PerpCR may be assigned to the first and/or second voxel.

In some embodiments, a grey matter voxel may be "matched" (i.e. combined) with more than one white matter voxel (or vice versa). In this case, an average would be calculated.

In some embodiments, the method comprises obtaining or determining values for both Axial Diffusivity and Perp in a plurality of voxels.

For example, values for Axial Diffusivity and Perp may be obtained or determined in 1-10,000, preferably 50-6,000, more preferably 100-500 voxels. For a whole-brain analysis, values for Axial Diffusivity may be obtained from 140,000-180,000, preferably about 160,000, white matter voxels and combined with values for Perp for the overlying grey matter voxels.

In some embodiments, the first and/or second voxels are ones which form a set of contiguous or semi-contiguous voxels which form a continuous or discontinuous arc across the cortex of the subject's brain.

The second voxel will lie beneath the first voxel in the radial direction. It does not need to be adjacent as the border region may be excluded. The second voxel (or set of voxels) will lie within the white matter of the same brain region as the grey matter containing the first voxel (or set of voxels) based on anatomical knowledge or on an automated assignment to regions using a probabilistic brain atlas, usually based on a prior database.

Optionally, the average value for the Perpendicular Columnar Refraction (PerpCR) for the selected voxels is determined using the average values for Axial Diffusivity and Perp in each of those voxels. Alternatively, some other mathematical function of Axial Diffusivity and Perp may be selected (e.g. weighted sum of Axial Diffusivity and Perp) to provide a value for Perpendicular Columnar Refraction (PerpCR).

Perpendicular diffusivity is the component of the diffusion occurring in the principal diffusion direction that is perpendicular to ColD. This can be measured by multiplying the main eigenvector (V1) by the value of its corresponding eigenvalue (L1), then resolving this into its components. The value of the component perpendicular to ColD is the perpendicular diffusivity.

In particular, a value for the perpendicular diffusivity (Perp) for the voxel may be obtained by projecting $D_{PDD}$ onto the plane which is orthogonal to ColD in that voxel and determining the magnitude of the projection. Perp is the value of this magnitude.

The term "PerpPD" may also be used interchangeably herein instead of "Perp".

As used herein, the term "provides an indication of the level of a cognitive disorder in that subject" means that there is a positive correlation between the value in question (e.g. AngleR, Axial Diffusivity, Perp, PerpCR or ACR) and the level of a cognitive disorder. Consequently, an increase in the value in question (compared to a value from a control healthy subject or compared to a previous value from that subject) means an increased likelihood or statistically-significant chance (where the increase is significant) of the subject having a cognitive disorder or a higher level of a cognitive disorder. The same applies to a decrease in the value, mutatis mutandis.

As used herein, the term "provides an indication of the number of microsegment breaks in that region" means that there is a positive correlation between the value in question (e.g. AngleR, Axial Diffusivity, Perp, PerpCR or ACR) and the number of microsegment breaks in that region. Consequently, an increase in the value in question (compared to a value from a control healthy subject or compared to a previous value from that subject) means an increased likelihood or statistically-significant chance (where the increase is significant) of the subject having microsegment breaks in that region or an increase in the number of microsegment breaks in that region. The same applies to a decrease in the value, mutatis mutandis.

In some embodiments, the method additionally comprises the step of positioning the subject in an MR scanner and obtaining MR diffusion data from the subject.

In other embodiments, the invention relates to a method of treatment, wherein the method additionally comprises the step: wherein, if the subject is found have a level of a cognitive disorder beyond (above or below) a specified reference level or is found to have a value for ACR or PerpCR above a specified reference level, a cognitive-disorder treating medicament is administered to the subject.

In other embodiments, the invention relates to a method of treatment, wherein the method comprises obtaining or receiving results of a method for determining ACR or PerpCR as disclosed herein, and if the ACR or PerpCR value is higher than a reference level, thereby providing an indication of the presence of a cognitive disorder in the subject, administering a treatment to the subject appropriate for treating the cognitive disorder.

In other embodiments, the invention relates to a computer-implemented method of obtaining an indication of the duration of a disease in a subject, wherein the disease is MS, the method comprising the steps of correlating:

(a) a measurement of the axonal fibre bundle width or a value derived therefrom in one or more regions of the subject's brain, with (b) the duration of the disease in the subject, wherein the measurement of axonal fibre bundle width or value derived therefrom is negatively correlated with the duration of the MS disease in the subject, thereby obtaining an indication of the duration of the MS disease in the subject.

In other embodiments, the invention relates to a computer-implemented method of obtaining an indication of the duration of a disease in a subject, wherein the disease is MS, the method comprising the steps of:

(i) comparing measurements of axonal fibre bundle widths or values derived therefrom from one or more regions of the brain of the subject, with (ii) a reference set of measurements of axonal fibre bundle widths or values derived therefrom from corresponding regions of the brains of control subjects with specific MS disease durations, wherein the measurement of axonal fibre bundle width or value derived therefrom is negatively correlated with the duration of the MS disease, thereby obtaining an indication of the duration of the MS disease in the subject.

In other embodiments, the invention relates to a computer-implemented method of obtaining an indication of the duration of a disease in a subject, wherein the disease is MS, the method comprising the step of:

(a) determining from a measurement of axonal fibre bundle widths obtained from one or more regions of the subject's brain, or values derived therefrom, an indication of the duration of the MS disease in the subject.

Preferably, the axonal fibre bundle width measurement is or was previously obtained by diffusion MRI. Preferably the brain region is area 41.

Where one or more measurements are taken, the average of the measurements may be used in the methods of the invention.

In a further embodiment, the invention provides a system or apparatus comprising at least one processing means arranged to carry out the steps of a method of the invention.

The processing means may, for example, be one or more computing devices and at least one application executable in the one of more computing devise. The at least one application may comprise logic to carry out the steps of a method of the invention.

The invention also provides the use of a system comprising at least one processing means arranged to carry out the steps of a method of the invention.

In a further embodiment, the invention provides a carrier bearing software comprising instructions for configuring a processor to carry out the steps of a method of the invention.

The disclosure of each reference set forth herein is specifically incorporated herein by reference in its entirety.

BRIEF DESCRIPTION OF THE FIGURES

FIG. 5: Correlations between histological Microsegments and a function of Axial Diffusivity and AngleR in two brain regions in post-mortem confirmed Alzheimer's disease and control brains.

FIG. 6: The difference between post-mortem confirmed Alzheimer's disease and control brains in the product of Axial Diffusivity and AngleR in two brain regions.

EXAMPLES

Figure 1A:
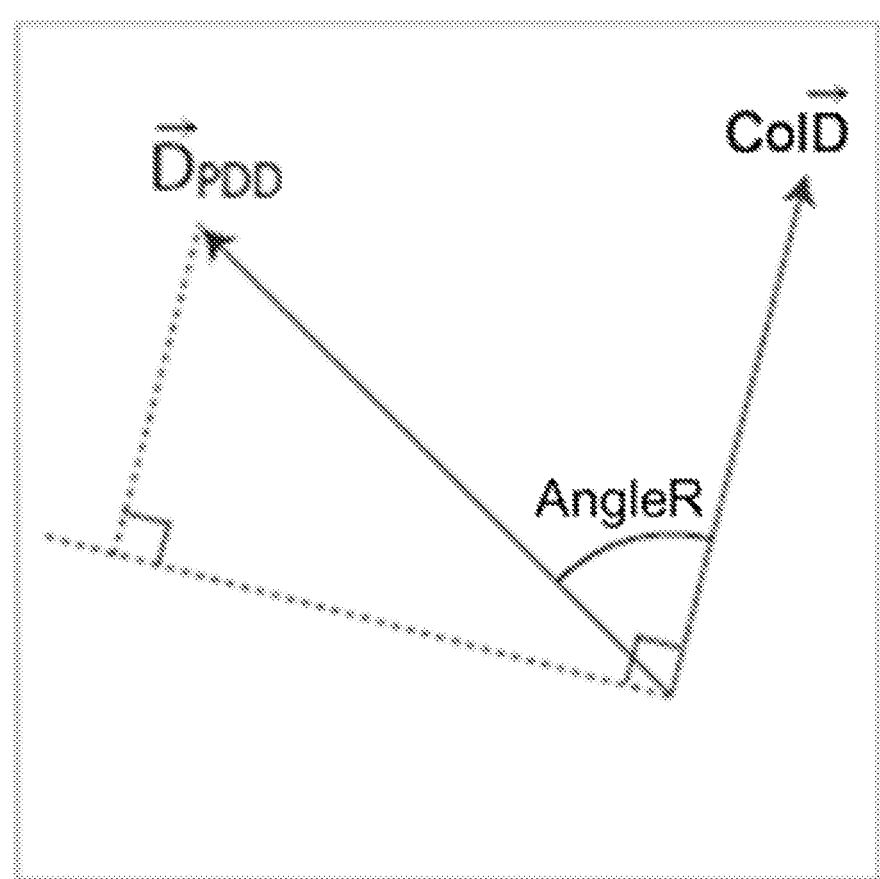
FIG. 1A. An illustrative voxel example of the derived diffusion-based measures. AngleR is averaged from the columnar set of voxels in the cortex.

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: Materials and Methods for Example 2

Ex-Vivo Brains

Brains were MRI scanned from 5 patients with a diagnosis of AD and 6 normally aged controls selected from the Oxford Brain Bank (OBB). The brains studied had been provided by donors from whom written informed consent had been obtained by the OBB for brain autopsy and use of material and clinical information for research purposes. Dementia brains were drawn from the Brains for Dementia Research network in the UK. Brains were extracted from the cranium and immersion fixed in a 10% neutral buffered formalin. The post-mortem interval (PMI) was 49.2±25.6 hours and the time before scanning (scan interval) was 59.1±39.9 weeks. Therefore the brains were not fixed for years, but had undergone fixation for a period of more than four weeks when the main shrinkage associated with fixation occurs (Quester & Schroder, 1997). Diagnosis of AD brains was confirmed by a clinical neuropathologist. Samples from different brain regions were taken for confirmation of diagnosis according to the criteria of the Consortium to Establish a Registry for Alzheimer's Disease (CERAD) and assigned a Braak score. Brains that showed substantial signs of other pathology, including Creutzfeldt-Jacob disease, Parkinson's disease, Lewy body disease, Huntington's disease, and cerebrovascular disease were excluded. No comorbidity of alcohol or illicit drug misuse was detected in our sample's records. This project was carried out with approval of the UK National Research Ethics Service, provided to the Oxford brain bank, and informed consent was obtained from all subjects and/or family representatives. The brains were scanned using modified acquisition suited to post-mortem tissue in order to derive structural and diffusion tensor imaging data.

Minicolumn Histological Analysis

After scanning and neuropathological sampling, brains were sectioned coronally. Blocks of size 25 mm×25 mm×10 mm were sampled for each of three regions from one hemisphere per brain (a representative sample of hemispheres: 4 left, 6 right). Due to constraints on availability of tissue from the brain bank, one dementia case was not accessible for the detailed histological sampling. For the 10 remaining cases, tissue blocks and the surrounding anatomy were photographed using an Olympus C-5050 digital camera for reference. The dorsolateral prefrontal cortex (dlPFC, area 9) ROI included the middle and superior frontal gyri bounded inferiorly at the paracingulate sulcus and inferior frontal sulcus. dlPFC blocks were sampled level with the cingulate gyrus. The inferior parietal lobe (area 40) was defined as the supramarginal gyrus, which is bounded superiorly by the intraparietal sulcus, inferiorly by the Sylvian fissure, anteriorly by the postcentral sulcus and posteriorly by the Jensen sulcus. The parahippocampal gyrus (PHG) was sampled within the limits defined posteriorly by the most posterior part of the hippocampus, anteriorly by the point where the hippocampus merges with the amygdala, and the superior boundary was the fusion between the hippocampus and the subiculum. For the PHG region two control cases were also not available, due to the high demand for medial temporal lobe samples for human brain studies. ROI selection was confirmed cyto-architecturally in accordance with Von Economo and Koskinas (1925).

Tissue blocks were embedded in paraffin wax and serially sectioned at 30 μm. Two sections were selected systematically randomly with respect to the limits of the tissue block and these were stained for the minicolumn analysis using cresyl violet Nissl stain (CV; ThermoFisher Scientific, Waltham, MA, USA).

Minicolumn width based on cell bodies was assessed using a semi-automated procedure that has been described in detail previously (Buxhoeveden et al., 2001; Casanova and Switala, 2005). This procedure gives a value for the minicolumn width consisting of the cell-dense core region plus the associated neuropil space surrounding it. Microsegment number was also measured as an index of disruption to minicolumn organisation by counting 'incomplete' minicolumn segments as described in Chance et al. (2011). For each ROI, three pictures were taken from a single microscope slide where possible, each containing a region of about 1 mm². Image locations were selected using a random number generator, excluding areas of high curvature which have been shown to affect cell distribution (Chance et al., 2004). As minicolumns are clearest in layer III, photographs were centred on that layer and obtained through a 4× objective lens, with an Olympus BX40 microscope (more details can be found in Di Rosa et al. (2009) and Van Veluw et al. (2012)). Values calculated from the three photographs were averaged to give a single value for each region.

Measuring Cortical Disruption Using DTI

Post-Mortem Scan Analysis

A novel analysis of MRI diffusion data was applied as a potential biomarker of neurodegeneration. We hypothesized that it would be sensitive to the cyto-architectural organisation of the cerebral cortex related to the minicolumn structure. Loss of synapses and neurites, followed by cell death, causes progressive damage to the normal organization of cortical neurons, producing altered cortical micro-geometry. We speculated that diffusion MRI may be sensitive to these effects, including the creation of minicolumn fragments (microsegments) through cell loss, minicolumn thinning, and disruption of axon and dendrite bundles. Cortical diffusivity analysis on post-mortem brains consisted of three stages: masking of the region of interest (ROI), calculation of the diffusion metrics within the ROI and extraction of the values for comparison with the histology measurements.

Cortical ROIs corresponding to those sampled histologically for minicolumn measurement were delineated using manually created masks on the structural MRI images (areas 9, 40 and PHG were identified using landmarks as described above). Careful comparison was also made with the photograph locations marked on the corresponding Nissl stained slide. Considering the reduced contrast between GM and WM tissue in post-mortem brains, due to fixation, the structural scan was overlaid with MD maps that had been co-registered previously in structural space, in order to include only grey matter voxels and avoid contamination from WM or CSF.

In order to calculate the diffusion metric values for each ROI, Cortical Disarray values were generated data from cortical profiles, i.e. lines in the cortex modelling the columnar arrays of cells that have migrated from the peri-ventricular region along radial glia and emerge from the white matter on top of each other to form the brain's cortical grey matter. These cortical profiles were generated by calculating the columnar direction based on neuroanatomy, with an origin in the white matter below the cortex, extending through the cyto-architecture of the cortical laminae to the pial surface. Values for the diffusion tensor-derived metrics were averaged along the cortical profiles, generating average values for each cortical profile.

Figure 1B:
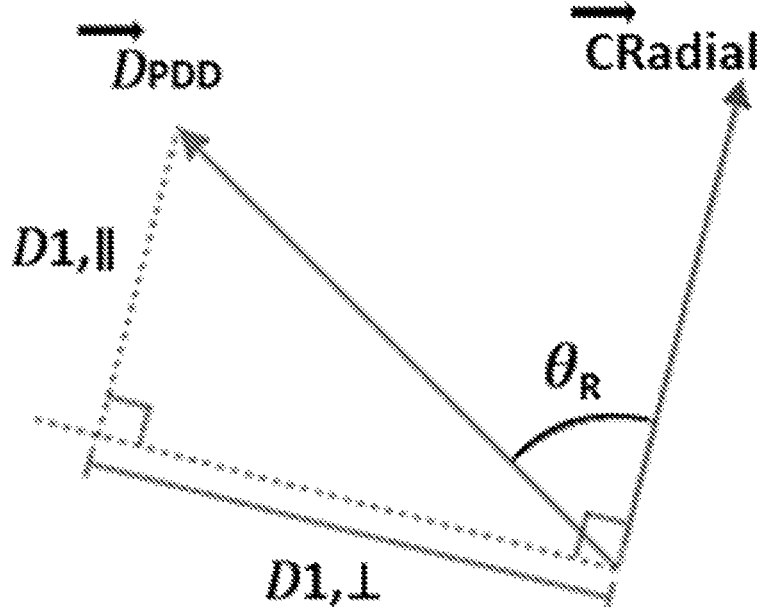
FIG. 1B. Example of the cortical diffusion data for one representative region (right), including an illustrative voxel example of the derived diffusion-based measures (left). The arrowed line towards $D_{PDD}$ indicates the principal diffusion vector in a voxel: on the right, only the direction is indicated, while on the left the diffusion tensor component along the PDD vector ($D_{PDD}$) is shown. The arrowed line towards CRadial indicates the radial direction normal to the cortex (CRadial). The angle of radiality, AngleR (notation $\theta_R$), in a voxel is the angle between the arrowed lines. The perpendicular diffusivity, PerpPD (notation D1, $\perp$), was calculated by projecting $D_{PDD}$ onto the plane perpendicular to CRadial. The parallel diffusivity, ParlPD (notation D1,//), was calculated by projecting $D_{PDD}$ onto the CRadial. Quantities were averaged along the radial cortical profile across the cortical layers, reflecting the minicolumnar organisation, as indicated for a set of voxels by the light line in FIG. 1C.
Figure 1C:
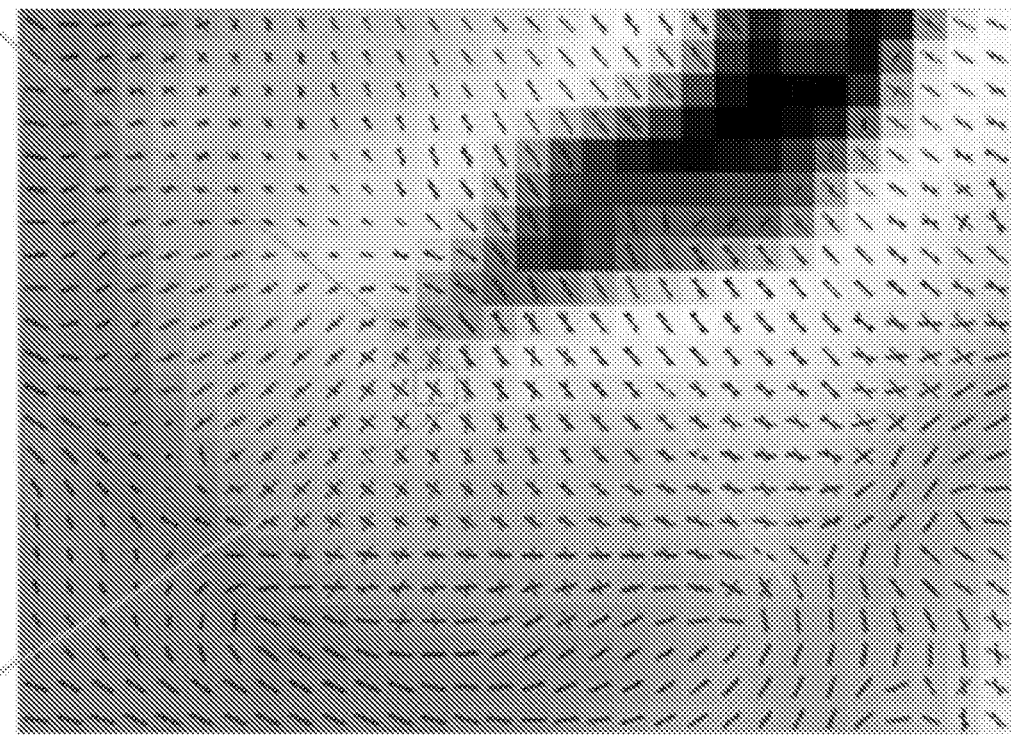

A mean for the tensor metric was then created by averaging the cortical profiles across each masked ROI, excluding the ends of the ROI (the first and last slices). Averages were calculated for FA, MD and a measure relating to the principal diffusion component, namely: the angle between the columnar direction and the principal diffusion direction, (AngleR). It was hypothesized that these measures were affected by variations in the organization and spacing of the radial barriers to diffusion provided by the cortical cyto-architecture. (It should be noted that the cortical diffusion assessments are not the same as axial and radial diffusivity—see FIG. 1).

A single ROI-average value for each diffusion metric enabled robustness against local noise/artifacts and also allowed for consistency with the histology measurements, which similarly calculated a single value for each ROI. Previous work has found that measures of the cyto- and myelo-architecture are relatively stable within a cortical region (e.g. Von Economo and Koskinas, 1925)) indicating that it is valid to find an average value for the region.

Exploratory In Vivo Dataset

In vivo data was based on a small pilot subset of previously collected scans from the ADNI dataset (Weiner et al., 2013): 15 controls and 14 AD. Controls scans came from 5 different centres and AD from 8 different centres. Assignment to diagnostic groups was enabled by clinical diagnosis, MMSE, and Clinical Dementia Rating scale (CDR) scores. Other conditions, including significant vascular disease, were ruled out, with Hachinski score less than 4. Data had been collected and provided with ethical approval according to the ADNI consortium guidelines.

For each subject, GM, WM, and CSF volumes were established using SPM8 segmentation, including computed GM fraction (GMf). For in vivo cortical diffusion validation the whole brain cortical grey matter mask was used initially to apply the cortical diffusion analysis. Then a region of interest analysis was applied to the same ROIs as were used for the post-mortem analysis: PHG, PFC, and Area 40.
Statistical Analysis All data were analyzed using SPSS v22 for Windows.

Due to the small sample size in the post-mortem diagnostic groups, the post-mortem data was used to compare the relationships between histology and DTI values within subjects while diagnostic group differences were investigated in the in vivo dataset. Significance thresholds were corrected for multiple comparisons.

The relationships between histology and DTI measures (including within-modality relationships) were investigated by correlation analysis using Pearson's correlation, or Spearman's Rank correlation for small groups. Of the neuropathological assessments, only Braak staging of tau positive neurofibrillary tangles was subjected to statistical analysis because it showed a range within and between groups.

Example 2: Results

Diagnostic Neuropathology

Figure 2:
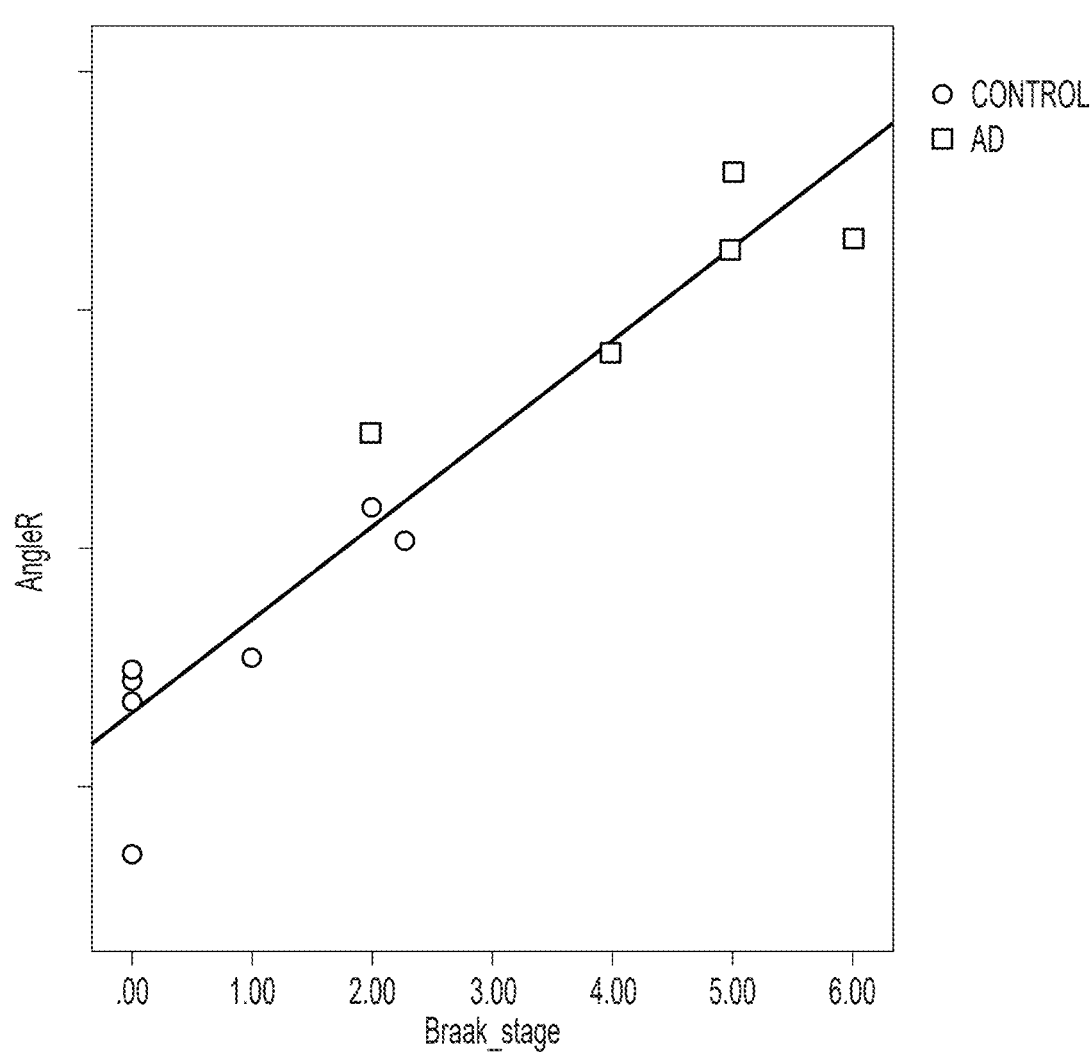
FIG. 2. The relationship between AngleR derived from post-mortem DTI data and the neuropathological gold standard for AD severity, Braak staging. Controls (circles, dotted linear regression line) and AD patient brains (squares, dashed linear regression line) have similar positive correspondence between AngleR and Braak staging.
Figure 3A:
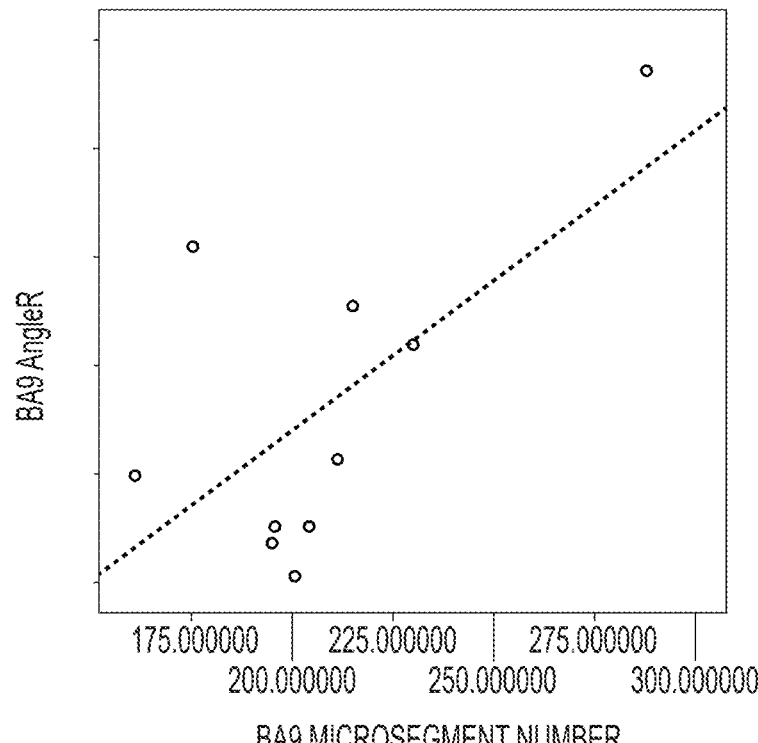
FIG. 3. The correlations between AngleR and microsegment number in two different brain regions.
Figure 3B:
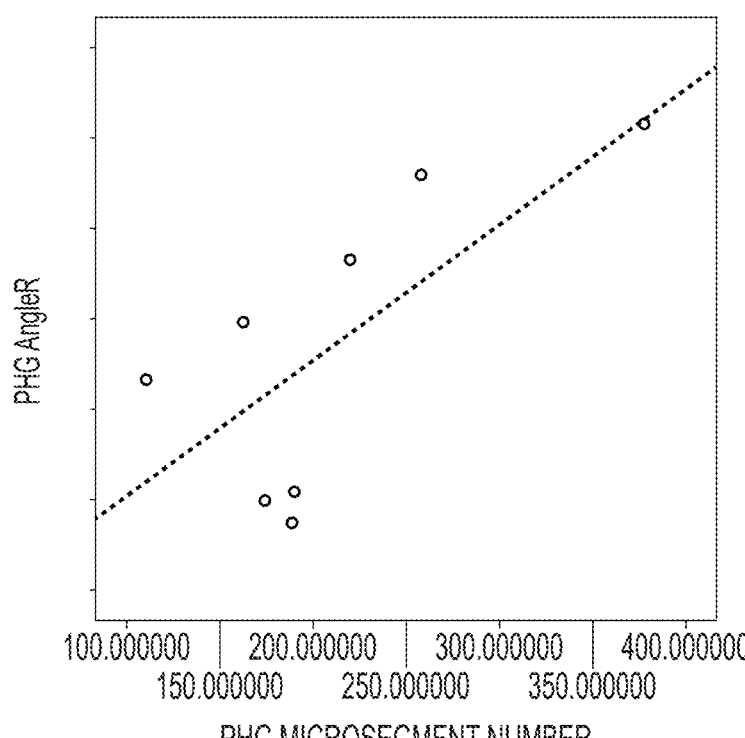

Braak staging was higher in AD brains compared with controls (Mann-Whitney U 0.5, p<0.01) (see distribution of values in FIG. 2). Other classifiers showed clear diagnostic category differences. CERAD classification was 'normal' for all control brains, whereas it was 'definite AD' or 'probable AD' for AD patients. BNET amyloid-B had a median value of 5 for AD brains and 1 for control brains.
Correlation Between DTI and Neuropathology Braak stage was positively correlated with AngleR in the PHG in control brains (Spearman's rho 0.85, p<0.05) and at a trend level in AD (Spearman's rho 0.82, p=0.09). Given the close match between best fit regression lines (see FIG. 2) it was apparent that there may be continuity between control and AD brains, which was also indicated by the overlap in Braak staging between the AD and controls. To consider this continuity, controls and AD were grouped together and a positive relationship between Braak staging and AngleR was present in all regions (PHG: Spearman's rho 0.96, p<0.001; Area 9: Spearman's rho 0.74, p=0.009; Area 40: Spearman's rho 0.61, p=0.045). FIG. 3.
Correlation between DTI and Histology A novel cortical diffusion value was hypothesized to relate to the horizontal spacing and integrity of minicolumns in the cortical grey matter: the angle of deviation from the estimated minicolumn direction (AngleR). The relationship between AngleR and histological minicolumn microsegment number and minicolumn width was examined by correlation testing.

There was a positive relationship between AngleR and microsegment number in all brain regions in AD, particularly in cortical areas 9 and PHG (Spearman's rho 1.0, p<0.01, for both).

The relationship was present across all subjects (see FIG. 3), although it was less clear in controls.

Figure 4A:
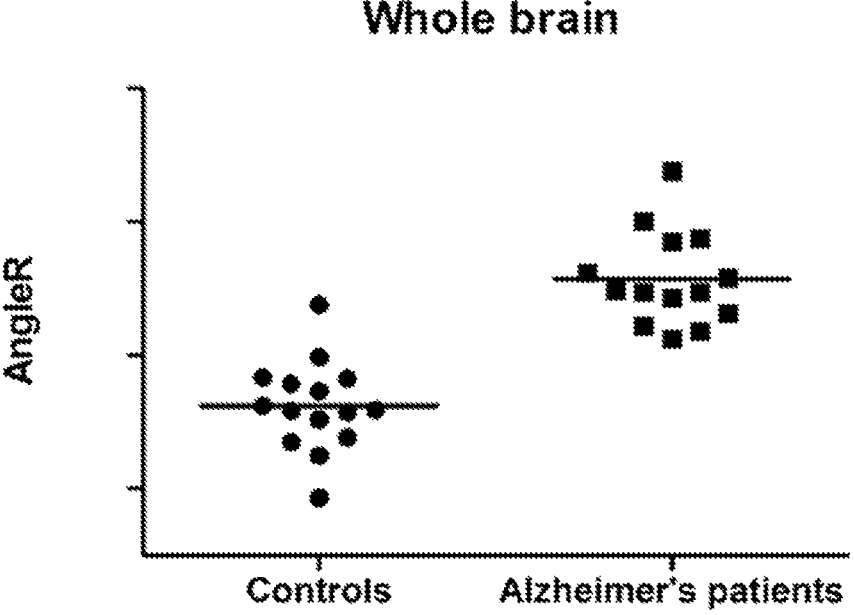
FIG. 4. The difference in AngleR (whole brain and sub-region PHG) between controls and AD in the trial in vivo dataset.
Figure 4B:
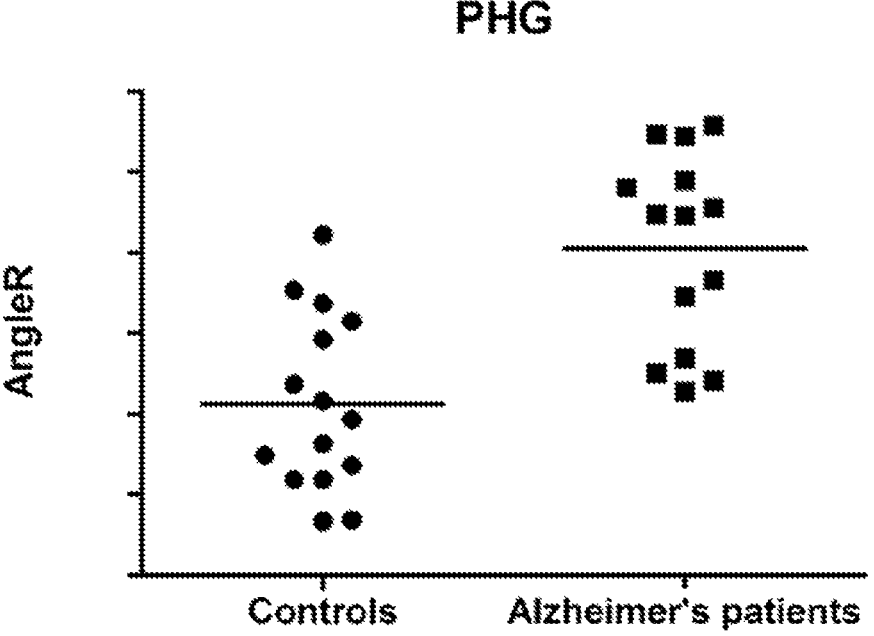
Figure 5A:
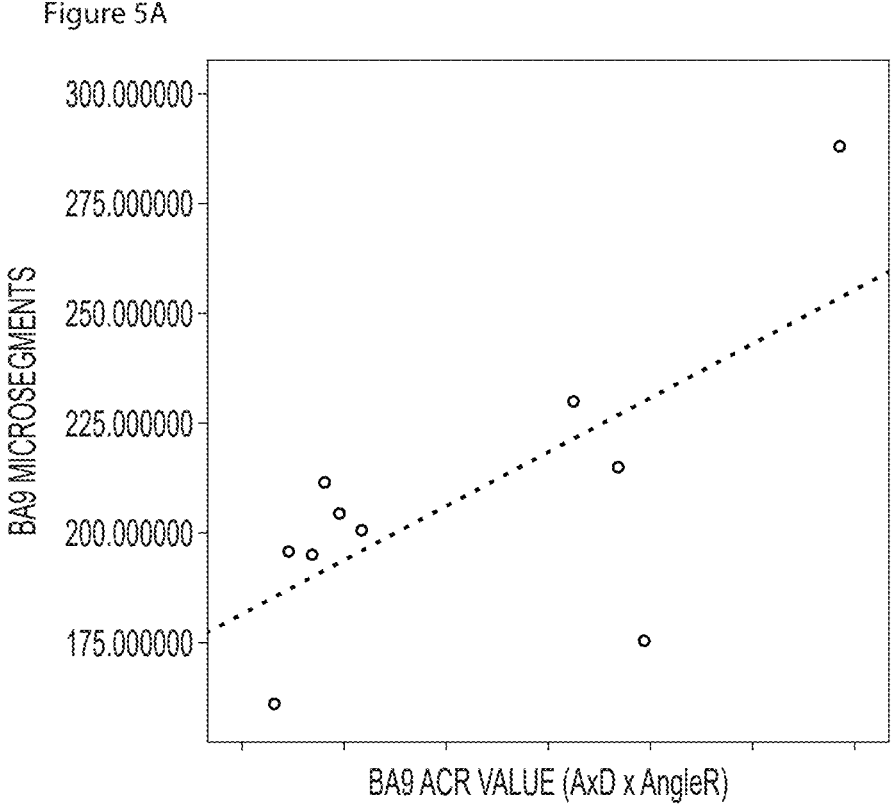
FIG. 5A—in prefrontal region (area 9).
Figure 5B:
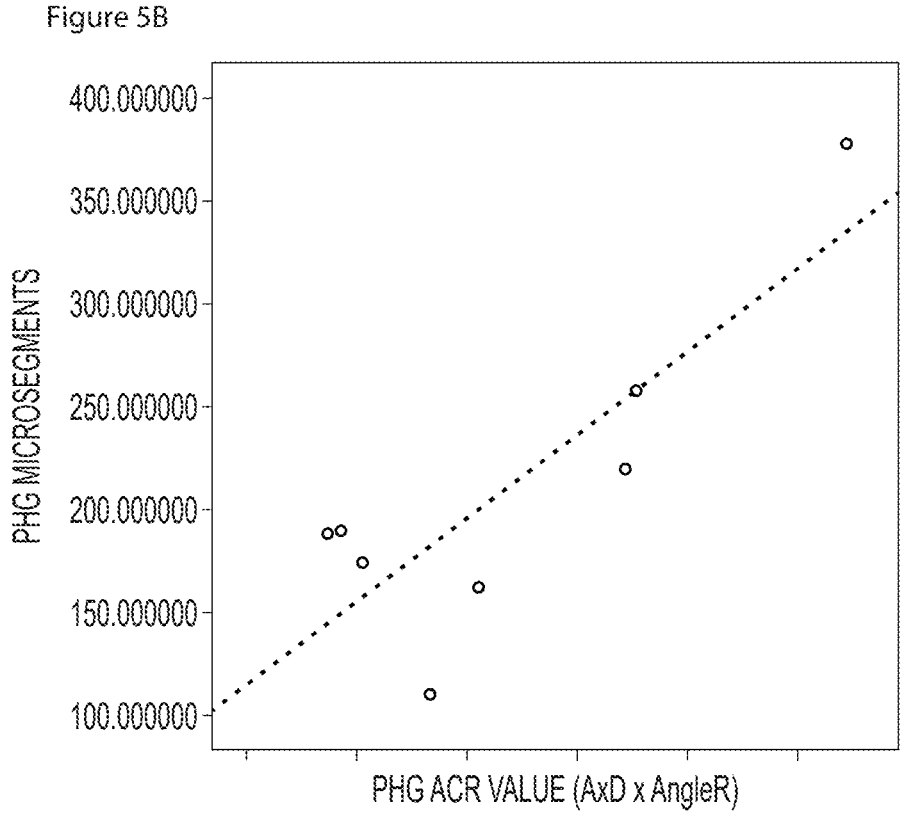
FIG. 5B—in medial temporal lobe (parahippocampal gyrus, PHG).
Figure 6A:
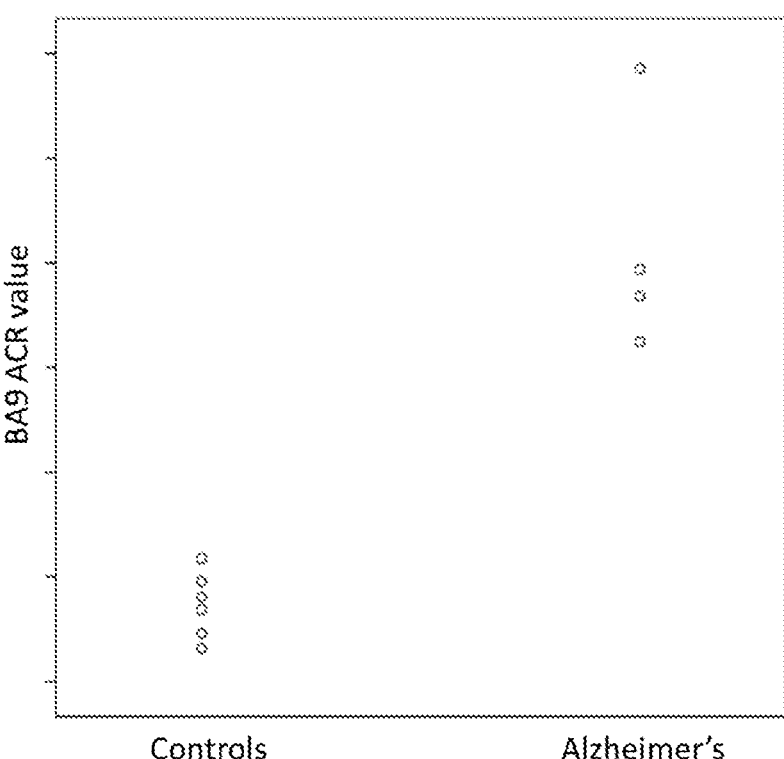
FIG. 6A—in prefrontal region (area 9).
Figure 6B:
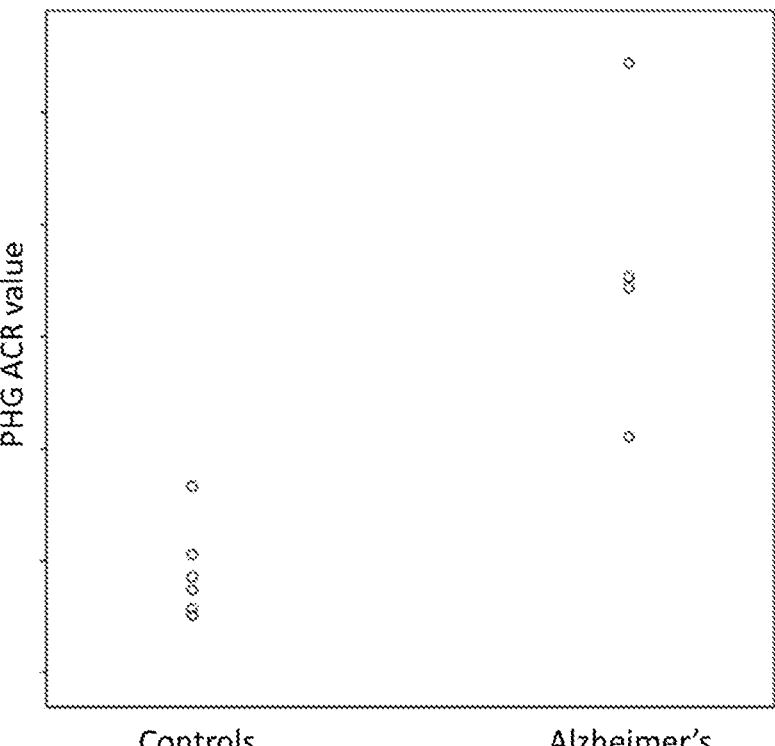
FIG. 6B—in medial temporal lobe (parahippocampal gyrus, PHG).

The measurements of FA and MD did not generally correlate with histological measures.
Demographic Correlates In general, the demographic variables, age, post-mortem interval, fixation time and brain weight did not show statistically significant correlations with the measured histological or cortical diffusion variables. Only one trend was observed; there was a non-significant indication of a positive association between age at death and AngleR in cortical area 9. The CDR value was 0 for all control subjects and a value of 3 for all AD patients except one who had a rating of 1.
In Vivo Cortical Diffusion Measurements For the whole brain analysis, an ANOVA found that AngleR was significantly higher in AD compared to controls (F 8.9, df 1.22, p<0.01), with age, subject movement, whole brain grey matter fraction, mean diffusivity and fractional anisotropy included as covariates. None of the covariates were statistically significant. (see FIG. 4 for AngleR).

For the ROI analysis, an ANOVA with 'brain region' as a repeated measure (PHG, PFC, Area 40) found that novel cortical diffusion values were significantly higher in AD compared to controls (F 6.4, df 1.22, p<0.02). The effect was most pronounced for AngleR in region PHG contributing to a trend for a measure x region effect (F 3.3, df 1.22, p=0.06). Age, subject movement, whole brain grey matter fraction, mean diffusivity and fractional anisotropy were included as covariates.

Example 3: Materials and Methods for Examples 4-5

Patients/Samples

Fixed whole brains from nine multiple sclerosis patients (Table 1) were obtained from the UK MS Tissue Bank (Imperial College, Hammersmith Hospital Campus, London). Brains were stored in 10% formalin before being transferred to a perfluorocarbon solution (Fomblin® LC08; Solvay Inc.; Bollate, Italy) for scanning, which contributes no MRI signal and provides susceptibility matching to tissue (reducing image artefacts).

TABLE 1

| Characteristics of brains provided for study. Multiple sclerosis cases (MS) and healthy controls (HC) | | | | | | | | | |
|---|---|---|---|---|---|---|---|---|---|
| Subject | Sex | Age | Hemisphere | Disease Progression | Disease Duration (yrs) | Time disease was progressive (yrs)[a] | Time in a wheelchair (yrs)[a] | Post-mortem Interval (hours) | Scan Interval (days) | Cause of Death |
| MS 254 | F | 69 | R | Secondary | 37 | 12 | 7 | 66 | 1198 | MS |
| MS 281 | F | 74 | L | Primary | 33 | | 17 | 40 | 929 | Sepsis |
| MS 314 | F | 78 | R | Secondary | 45 | 24 | 17 | 60 | 435 | Colonic carcinoma |
| MS 316 | F | 79 | R | Secondary | 55 | 40 | 36 | 26 | 1052 | Pneumonia |
| MS 322 | M | 72 | L | Secondary | 28 | 4 | | 59 | 1201 | Pneumonia |
| MS 332 | F | 50 | R | Secondary | 22 | 10 | 2 | 69 | 1134 | Breast cancer mets |
| MS 334 | M | 66 | R | Secondary | 15 | | 1 | 37 | 1126 | Prostate cancer |
| MS 396 | F | 86 | R | Primary | 54 | | | 54 | 578 | Lymphoma |

TABLE 1-continued

Characteristics of brains provided for study. Multiple sclerosis cases (MS) and healthy controls (HC)

| Subject | Sex | Age | Hemisphere | Disease Progression | Disease Duration (yrs) | Time disease was progressive (yrs)[a] | Time in a wheelchair (yrs)[a] | Post-mortem Interval (hours) | Scan Interval (days) | Cause of Death |
|---------|-----|-----|------------|---------------------|------------------------|----------------------------------------|-------------------------------|------------------------------|----------------------|----------------|
| MS 400 | F | 60 | L | Secondary | 11 | | 7 | 21 | 539 | MS |
| HC 1 | M | 72 | R | — | — | — | — | 24 | 693 | |
| HC 2 | F | 88 | R | — | — | — | — | 24 | 655 | |
| HC 3 | M | 68 | R | — | — | — | — | 48 | 1236 | |
| HC 4 | F | 82 | L | — | — | — | — | 48 | 1197 | |
| HC 5 | F | 68 | L | — | — | — | — | 48 | 1216 | Pancreas carcinoma |
| HC 6 | F | 48 | R | — | — | — | — | 48 | 1151 | Pneumonia |

[a]MS clinical details where data was not available for all cases

MRI Scanning

Nine multiple sclerosis patients and six control brains from a pre-existing cohort in the Oxford Brain Bank, were used for the MRI comparison. Scanning was carried out on a Siemens Trio 3T scanner using a 12-channel head coil. Scanning was conducted at room temperature and each scan session lasted approximately 24 hours. Diffusion weighted data were acquired using a modified spin-echo sequence with 3D segmented EPI (TE/TR=122/530 ms, bandwidth=789 Hz/pixel, matrix size: 168×192×120, resolution 0.94×0.94×0.94 mm). Diffusion weighting was isotropically distributed along 54 directions (b=4500 s/mm2) with six b=0 images. This protocol takes approximately 6 hours, and three averages were acquired for 18 hours total diffusion imaging. Structural scans were acquired using a 3D balanced steady state free precession (BSSFP) sequence (TE/TR=3.7/7.4 ms, bandwidth=302 Hz/pixel, matrix size: 352× 330×416, resolution 0.5×0.5×0.5 mm). Images were acquired with and without RF phase alternation to avoid banding artefacts. This was averaged over eight repeats to increase signal to noise ratio. For more details see Miller et al. (2011).

Data was processed using the FMRIB software library (FSL) (Smith et al., 2004; Woolrich et al., 2009). The FSL diffusion toolbox was used to process diffusion weighted data, which incorporates an in house processing pipeline to compensate for gradient-induced-heating drift and eddy-current distortions, to produce maps of fractional anisotropy (FA), mean diffusivity (MD) and the diffusion tensor components (Miller et al., 2011).

Selection of Brain Regions

Measures of cortical thickness in dorsolateral prefrontal cortex (Area 9) and primary visual cortex (V1) and diffusion measures of connected white matter tracts (FA and MD) were correlated with histological myelination measures in our previous study (Kolasinski et al., 2012) and, as multiple sclerosis is a demyelinating disorder, these areas were chosen for further investigation in the present study. In addition, these areas are well characterised and are known to represent a range of cortical cyto-architectural arrangements (i.e. wider minicolumns in Area 9 and narrower minicolumns in V1). An additional comparison region was included—the primary auditory cortex within Heschl's gyrus (Area 41)—because its columnar architecture is well characterised but there have been inconsistencies in previous reports on its PDD in healthy subjects (Kang et al., 2012; McNab et al., 2013). Investigation of multiple cortical regions allowed us to explore the sensitivity of diffusion metrics to regional differentiation, which would be of interest in future investigations of neurological disorders.

Neurohistological Sampling

Brains were sectioned coronally and the diagnosis of multiple sclerosis was confirmed by a clinical neuropathologist. Blocks of size 25 mm×25 mm×10 mm were sampled for each of the three regions from one hemisphere per brain (a representative random sample of hemispheres: 7 left, 8 right). Blocks and the surrounding tissue were photographed using an Olympus C-5050 digital camera for reference. Area 9 included the middle and superior frontal gyri bounded inferiorly at the paracingulate sulcus and inferior frontal sulcus. Area 9 blocks were sampled level with the anterior limit of the cingulate gyrus. Area 41 blocks incorporated Heschl's gyrus, bordered medially by the insula cortex and laterally by the planum temporale. V1 blocks were sampled along the calcarine fissure, level with the medium transverse occipital gyrus. Region of interest (ROI) selection was confirmed cyto-architecturally in accordance with Von Economo and Koskinas (1925).

Tissue blocks were embedded in paraffin wax and serially sectioned at 10 μm for the minicolumn analysis and quantification of myelin levels, and at 30 μm for the bundle measurements. Sections were stained with cresyl violet (CV; ThermoFisher Scientific, Waltham, MA, USA) for minicolumn analysis, anti-proteolipid protein stain (AbD AbSerotec, Oxford, UK) (anti-PLP) for light transmittance myelin quantification, and Sudan black, a myelin sensitive lipophilic dye, for measurement of axonal bundles.

Cortical Diffusivity Analysis

This was a region-of-interest approach. Cortical ROIs corresponding to those sampled histologically were delineated using manually created masks on the structural post-mortem images. By careful reference to photographic images of the physically cut coronal brain slice before and after the tissue block was removed, and the corresponding Nissl stained slide, the closest matching coronal slice of the structural MRI scan was identified. Cortical ROIs were masked over 15 coronal slices of the MRI image centred around this slice, taking care to include only grey matter voxels to avoid contamination from white matter or CSF. The limits of the cortical ROIs were determined by careful comparison with the photographic images and corresponding Nissl stained slide in order to ensure the masked area matched the histologically sampled area. Novel software scripts (Mark Jenkinson, University of Oxford, 2018; WO2016/162682A1; U.S. patent application Ser. No. 15/564,344) were used to generate cortical profiles on the MRI scans, i.e. lines across the cortex in a radial direction, replicating a columnar organisation within the cortex. Values for the diffusion tensor derived metrics were averaged along the cortical profiles, across the entire masked ROI, excluding the terminal slices at the anterior and posterior ends of the RO. The metrics calculated were MD, FA and three metrics relating to the principal diffusion component (see also WO2016162682A1; U.S. patent application Ser. No. 15/564,344), namely: the angle of the deviation between the radial direction across the cortical layers and the principal diffusion direction (AngleR, $\theta_R$); the principal diffusion component projected onto the plane perpendicular to the radial direction across the cortex (described therefore as the perpendicular diffusivity, i.e. PerpPD, D1,$\perp$ ($\times$10-3 mm2/ sec)), and the principal diffusion component projected onto the radial direction across the cortex (described therefore as parallel to the radial direction, i.e. ParlPD, D1,$\parallel$ ($\times$10-3 mm2/sec).

Averaging values reduced the influence of noise in the DTI data, effectively smoothing the data, and ensuring only directionality with some local coherence would dominate, guarding against the influence of random deflections from the radial direction. Averaging also provided consistency with the histological measurements, which similarly calculated a single value for each cortical region. Previous work has found that measures of the cyto- and myelo-architecture are relatively stable within a cortical subregion (e.g. Von Economo and Koskinas (1925)) indicating that it is valid to find an average value for that region.

Minicolumn Analysis

Minicolumn width, based on cell bodies, was assessed in the histological tissue sections using a semi-automated procedure that has been described in detail previously (Buxhoeveden et al., 2001; Casanova and Switala, 2005). This procedure gives a value for the minicolumn width consisting of the cell dense core region plus the associated neuropil space surrounding it. The neuropil spacing is the width of the cell sparse neuropil region between the cores of neighbouring minicolumns, while the core refers to the width of the cell dense region at the centre of the minicolumn. The microsegment number is the number of strings of cells that do not form a complete minicolumn because they are discontinuous with the rest of a minicolumn due to it passing out of the plane of section or due to minicolumn fragmentation as a result of pathology. Cell density refers to the density of cells recognised by the automated histology analysis programme within the field of view of each assessed digital photomicrograph. (See Chance et al 2011 for further discussion of microsegments and cell density) For each ROI, three digital photomicrographs were taken from a single slide where possible, each containing a region of about 1 mm$^2$. Image locations were selected using a random number generator, excluding areas of high curvature which have been shown to affect cell distribution (Chance et al., 2004). As minicolumns are clearest in layer III, photographs were centred on that layer and obtained through a 4$\times$ objective lens, with an Olympus BX40 microscope (more details can be found in Di Rosa et al. (2009) and Chance et al. (2004)). Values calculated from the three photographs were averaged to give a single value for each region.

Quantification of Myelin Levels

Cortical myelin content was assessed using light transmittance to quantify the intensity of myelin stain in anti-PLP stained tissue sections. Data were collected using Axiovision v4.7.2 software on a PC receiving a signal from an Axiocam MRc (Carl-Zeiss, Jena, Germany) mounted on a BX40 microscope (Olympus. Japan) with a 10$\times$ objective lens. The set up was calibrated in RGB mode with fixed white balance and incident light, using a standard slide/coverslip preparation and light filters (6%, 25% and 100% transmittance). For each ROI three measures of transmittance (T) were taken in different locations across layers III to V using a 58,240 $\mu$m$^2$ virtual frame on anti-PLP stained sections and the resulting values averaged.

Axon Bundle Analysis

For each region three photographs were obtained through a 10$\times$ objective lens (resolution 1.10 $\mu$m) with an Olympus BX40 microscope, centred around layer V as the axon bundles are clearest there. Areas of extreme curvature were avoided where possible, as was done for the minicolumn measurements.

Measurements of axon bundle centre-to-centre spacing, and the width of the bundles themselves were made manually in Axiovision, using the in-built measurement tools. The digital resolution of the analysed images was 0.67 $\mu$m/pixel. A sample line of standard length (590 $\mu$m; determined by the size of the image view) was drawn across the centre of the photograph, perpendicular to the bundle direction in order to identify the bundles to be measured. Only bundles intersecting this line were measured, those that passed out of the plane of sectioning above or below the line were not included. Single axons or pairs of axons crossing the line were not considered to constitute axon bundles for the purposes of this analysis.

Bundles (>2 axons) were identified and their centres marked. Bundle spacing measurements were then made from the centre of each bundle marked in this way to the centre of the adjacent bundle. The width of each axon bundle was also measured. For the width measurements, the edges of the bundles were marked at the point where they intersected the line, and the bundle width was determined as the distance between these two points. Edges of axon bundles were distinguished by the change in intensity of staining from the background, which identified the start of the more darkly stained axon bundle. Pilot data revealed high reliability of this method, finding a high correlation (r=0.737, p<0.001) between measurements of photos taken on two different occasions. The values from the three photographs were then averaged to give a single value for bundle spacing and a single value for bundle width for each ROI.

This resulted in an average of 28 ($\pm$5), 22 ($\pm$5), and 44 ($\pm$5) bundles being sampled for Area 9, Area 41 and V1 respectively for each subject. It was not possible to assess the orientation of the axon bundles within the cortex in a manner directly comparable to our DTI analysis because such a three-dimensional estimate is not possible in histological sections that have a limited depth, compounded by z-direction compression on the microscope slide. However, taking a subset of cases with a relatively un-curved section of cortex where it may be assumed that the three-dimensional geometric vertical is reasonably close to the two-dimensional estimate from the histological section, we were able to measure the orientation of the axon bundles relative to this. This indicated that the axon bundles deviate from the radial direction across the cortex by an average of 3.50 ($\pm$2.68) degrees.

Statistical Analysis

All data were analysed using SPSS v22 for Windows and the R statistical package (version 3.3.3) (R Core Team, 2013).

Relationship between histology and DTI—The relationship between the microanatomy and MRI diffusion metrics across the full data set was investigated by correlation analysis using Spearman's Correlation Coefficient. We carried out a correlation analysis for each of the 3 regions of interest (Area 9, Area 41 and V1) including the 5 diffusion metrics (FA, MD, Angle_R, PerpPD, ParlPD) and the 6 histology measures (Minicolumn width, Core width, Neuropil Spacing, Microsegment number, Axon bundle width, Bundle spacing). All p-values were adjusted with false (ParlPD is the component of the principal diffusion vector that was parallel to the radial minicolumn direction across the cortex.)

TABLE 2

Mean values for histological variables for each region in
MS brains. Standard deviations are given in brackets.

| Regions | Minicolumn Width (µm) | Minicolumn Spacing (µm) | Minicolumn Core width (µm) | Minicolumn Microsegment number/mm² | Cell Density | Axon Bundle Spacing (µm) | Axon Bundle Width (µm) |
|---|---|---|---|---|---|---|---|
| Area 9 | 37.7 | 15.5 | 28.9 | 203.5 | 123.1 | 45.3 | 8.2 |
| | (2.50) | (2.07) | (4.16) | (103.66) | (42.53) | (3.74) | (1.33) |
| Area 41 | 33.7 | 16.1 | 27.8 | 203.4 | 146.3 | 48.3 | 9.6 |
| | (4.14) | (1.10) | (2.61) | (40.56) | (49.82) | (6.82) | (0.70) |
| V1 | 27.1 | 15.5 | 26.7 | 247.7 | 95.8 | 28.6 | 7.3 |
| | (3.38) | (1.59) | (3.33) | (64.39) | (48.06) | (3.94) | (0.84) | discovery rate correction (FDR<0.05) (Benjamini & Yekutieli., 2001) and were reported using the approach of Preziosa et al. (2019) by providing p and $P_{FDR}$ for significant results.

Mean regional differences—Regional differences in both histology and DTI metrics within groups were assessed using repeated measures ANOVAs and significant main effects were followed up with post-hoc t-tests. Regional differences in DTI between groups were assessed using repeated measures ANOVA.

Histology measures—Relationships between the 6 histology measures (Minicolumn width, Core width, Neuropil Spacing, Microsegment number, Axon bundle width, Bundle spacing) were investigated using Spearman's Correlation Coefficient and adjusted by FDR correction (FDR<0.05)

Multiple sclerosis clinical correlates—Our previous study indicated a relationship between the degree of change in white matter and cellular organisation in Area 9 and V1 (Kolasinski et al., 2012). As disease duration was the only clinical measure available for all subjects (Table 1), the present study investigated whether there was a significant correlation between DTI derived metrics and disease duration in these cortical regions (Area 9 and V1), and whether the correlations were different to that in the comparison region (Area 41). As age was expected to correlate with disease duration this was controlled for where appropriate using partial correlations using the standard SPSS recursive algorithm.

Example 4: DTI Differences Between Groups and Brain Regions

We used a pre-existent cohort of six controls to investigate the diffusivity measures between groups. Repeated measures ANOVAs revealed a significant main effect of diagnosis on diffusion metrics, (Tables 2, 3): AngleR ($F_{1,13}$=15.575, p=0.002), MD ($F_{1,13}$=20.468, p=0.002), PerpPD ($F_{1,13}$=39.177, p=0.000), and ParlPD ($F_{1,13}$=16.905, p=0.001) values were higher in multiple sclerosis cases compared to controls in all regions, while FA was not different between groups ($F_{1,13}$=0.928, p=0.353). There was also a within subjects effect of region (FIG. 7) due to higher AngleR values in V1 compared to other regions ($F_{2,26}$=5.512, p=0.026) (the region difference was slightly greater in controls but there was no region x diagnosis interaction). No significant differences between regions were found within subjects for FA, MD, PerpPD or ParlPD.

TABLE 3

Mean values for diffusion measures for each region in MS brains
and controls. Standard deviations are given in brackets.

| | Regions | FA | MB | AngleR | PerpPD | ParlPD |
|---|---|---|---|---|---|---|
| MS cohort | Area 9 | 0.0712 | 0.320* | 0.898* | 0.163* | 0.334* |
| | | (0.02) | (0.09) | (0.09) | (0.05) | (0.24) |
| | Area 41 | 0.0909 | 0.435* | 0.868* | 0.179* | 0.101* |
| | | (0.02) | (0.07) | (0.15) | (0.20) | (0.03) |
| | V1 | 0.0875 | 0.251* | 0.911* | 0.139* | 0.113* |
| | | (0.03) | (0.05) | (0.13) | (0.04) | (0.04) |
| HC cohort | Area 9 | 0.0925 | 0.190 | 0.679 | 0.075 | 0.138 |
| | | (0.02) | (0.03) | (0.02) | (0.02) | (0.02) |
| | Area 41 | 0.1018 | 0.120 | 0.677 | 0.057 | 0.081 |
| | | (0.02) | (0.01) | (0.03) | (0.01) | (0.02) |
| | VI | (0.0916) | 0.164 | 0.821# | 0.073 | 0.085 |
| | | (0.03) | (0.03) | (0.06) | (0.01) | (0.03) |

*= value significantly higher than HC in between group comparison;
= value significantly higher than other regions in within group comparison.

Example 5: Histology Differences Between Brain Regions

Figure 7:
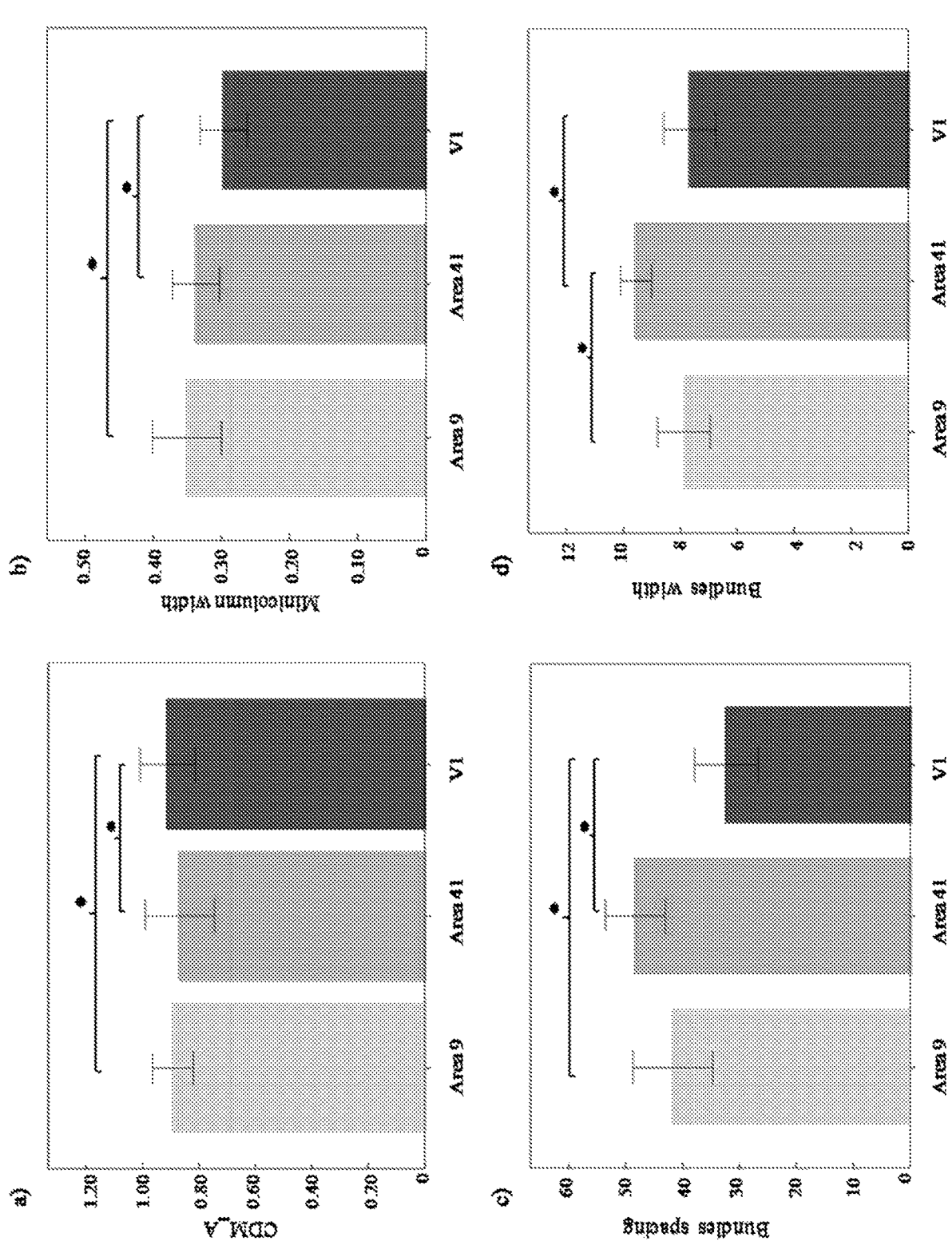
FIG. 7: Regional differences in a) AngleR, b) minicolumn width, c) axon bundle spacing, and d) axon bundle width. Error bars show standard deviations.

Repeated measures ANOVA revealed a significant main effect of region on all histological measures (Tables 2, 3; FIG. 7). Primary visual cortex had the narrowest minicolumns and narrowest axon bundles, with Area 41 having the widest spacing of axon bundles and the widest bundles.

Example 6: Relationships with Clinical Variables

Figure 8:
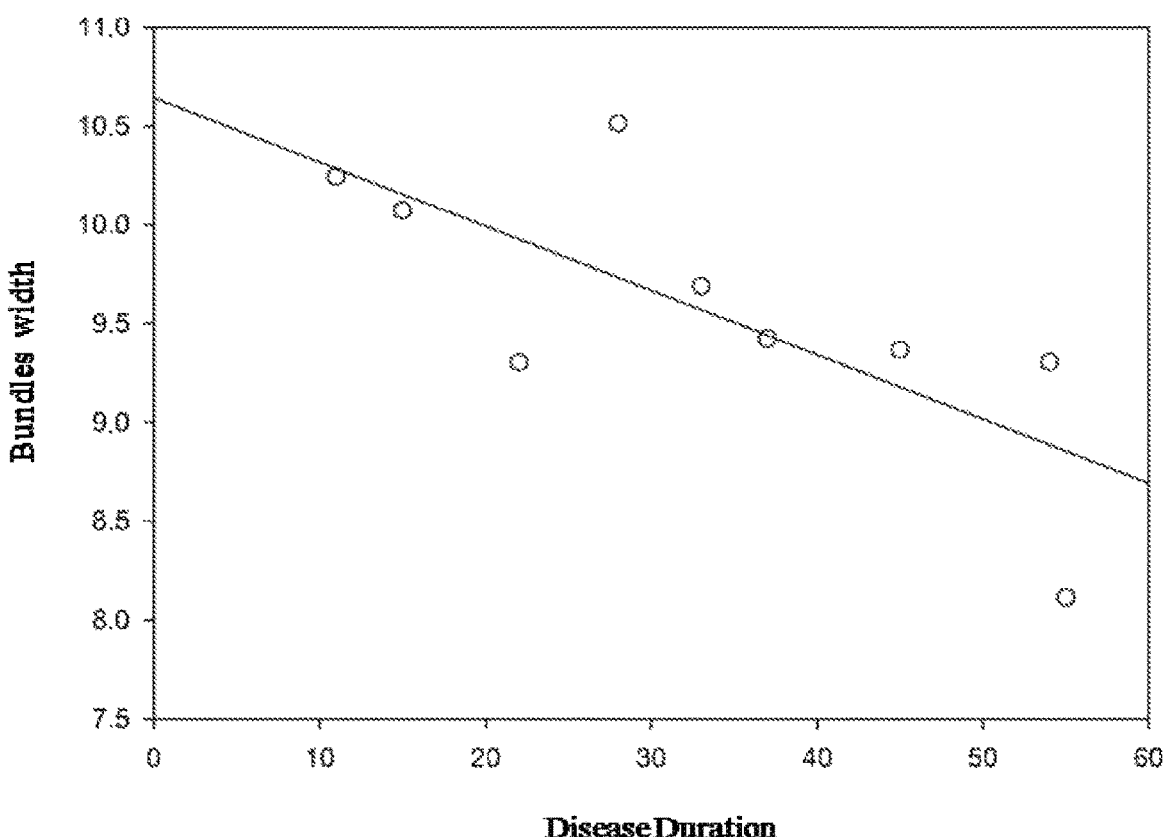
FIG. 8: Relationship between bundle width and disease duration in primary auditory cortex in MS brains.

Due to the presence of a strong correlation between disease duration and age (r=0.883, p=0.002) partial correlations controlling for age were used to investigate the relationships with disease duration. A significant negative correlation was observed between bundle width and disease duration in Area 41 (r=−0.867, p=0.011) (FIG. 8) but not Area 9 (r=−0.438, p=0.278) or V1 (r=−0.077, p=0.856).

REFERENCES

Esiri, M. M.; Chance, S. A. Vulnerability to Alzheimer's pathology in neocortex: The roles of plasticity and columnar organization. Journal of Alzheimer's Disease 9(Suppl 3): 79-89 (2006)

Chance, Steven A.; Clover, Linda; Cousijn, Helena; et al. Microanatomical Correlates of Cognitive Ability and Decline: Normal Ageing, MCI, and Alzheimer's Disease. Cerebral Cortex 21(8) Pages: 1870-1878 (2011)

Chance S. A.; Casanova M. F.; Switala A. E.; Crow T. J.; Esiri M. M. Minicolumn thinning in temporal lobe association cortex but not primary auditory cortex in normal human ageing. Acta Neuropathologica 111(5): 459-64 (2006)

Ioan Opris Manuel F. Casanova. Prefrontal cortical minicolumn: from executive control to disrupted cognitive processing. Brain, Volume 137, Issue 7, 1 Jul. 2014, Pages 1863-1875(2014)

Quester R, Schroder R. The shrinkage of the human brain stem during formalin fixation and embedding in paraffin. J Neurosci Methods 75:81-89. (1997)

Von Economo C, Koskinas G N. Die Cytoarchitektonik der Hirnrinde des Erwachsenen Menschen. Springer, Berlin (Germany); 1925.

Buxhoeveden D P, Switala A E, Litaker M, Roy E, Casanova M F. Lateralization of minicolumns in human planum temporale isabsent in nonhuman primate cortex. Brain Behav Evol 2001; 57:349-58

Casanova M F, Switala A E. Minicolumnar Morphometry: Computerized Image Analysis. In: Casanova M F, editor. Neocortical Modularity and the Cell Minicolumn. New York:Nova Biomedical; 2005. p. 161-80.

Chance, S A; Tzotzoli, P M; Vitelli, A; Esiri, M M; Crow, T J. The cytoarchitecture of sulcal folding in Heschl's sulcus and the temporal cortex in the normal brain and schizophrenia: lamina thickness and cell density. Neuroscience Letters 367 (3): 384-388 (2004)

Di Rosa E, Crow T J, Walker M A, Black G, Chance S A (2009) Reduced neuron density, enlarged minicolumn spacing and altered ageing effects in fusiform cortex in schizophrenia. Psychiatry Res 166:102-115 van Veluw, S J; Sawyer, E K; Clover, L; Cousijn, H; De Jager, C; Esiri, M M Esiri; Chance, S A. Prefrontal cortex cytoarchitecture in normal aging and Alzheimer's disease: a relationship with IQ. Brain Structure & Function 217(4): 797-808 (2012)

Weiner, M. W., Veitch, D. P., Aisen, P. S., Beckett, L. A., Cairns, N. J., Green, R. C., Alzheimer's Disease Neuroimaging Initiative. (2013). The Alzheimer's Disease Neuroimaging Initiative: A review of papers published since its inception. Alzheimer's & Dementia: The Journal of the Alzheimer's Association, 9(5), e111-e194.

ADDITIONAL REFERENCES

Andersson J L R, Graham M S, Zsoldos E, Sotiropoulos S N. (2016). Incorporating outlier detection and replacement into a non-parametric framework for movement and distortion correction of diffusion M R images. Neuroimage, 141, 556-572.

Anwander, A., Pampel, A., & Knosche, T. R. (2010). In vivo measurement of cortical anisotropy by diffusion-weighted imaging correlates with cortex type. In Proc. Int. Soc. Magn. Reson. Med (Vol. 18, p. 109).

Benjamini, Y., & Yekutieli, D. (2001). The control of the false discovery rate in multiple testing under dependency. Annals of statistics, 1165-1188.

Barazany, D., & Assaf, Y. (2011). Visualization of cortical lamination patterns with magnetic resonance imaging. Cerebral Cortex, 22(9), 2016-2023.

Beaulieu, C. (2002). The basis of anisotropic water diffusion in the nervous system—a technical review. NMR in Biomedicine, 15(7-8), 435-455.

Buxhoeveden, D. P., & Casanova, M. F. (2002). The minicolumn hypothesis in neuroscience. Brain, 125(5), 935-951.

Buxhoeveden, D. P., Switala, A. E., Litaker, M., Roy, E., & Casanova, M. F. (2001). Lateralization of minicolumns in human planum temporale is absent in nonhuman primate cortex. Brain, Behavior and Evolution, 57(6), 349-358.

Casanova, M. F., Buxhoeveden, D. P., Switala, A. E., & Roy, E. (2002). Minicolumnar pathology in autism. Neurology, 58(3), 428-432.

Casanova, M. F., Konkachbaev, A. I., Switala, A. E., & Elmaghraby, A. S. (2008). Recursive trace line method for detecting myelinated bundles: a comparison study with pyramidal cell arrays. Journal of neuroscience methods, 168(2), 367-372.

Casanova, M. F., & Switala, A. E. (2005). Minicolumnar morphometry: computerized image analysis. Neocortical modularity and the cell minicolumn. Nova Biomedical, New York, 161-180.

Chance, S. A., Casanova, M. F., Switala, A. E., Crow, T. J., & Esiri, M. M. (2006). Minicolumn thinning in temporal lobe association cortex but not primary auditory cortex in normal human ageing. Acta neuropathologica, 111(5), 459-464.

Chance, S. A., Sawyer, E. K., Clover, L. M., Wicinski, B., Hof, P. R., & Crow, T. J. (2013). Hemispheric asymmetry in the fusiform gyrus distinguishes *Homo sapiens* from chimpanzees. Brain Structure and Function, 218(6), 1391-1405.

Chance, S. A., Casanova, M. F., Switala, A. E., & Crow, T. J. (2008). Auditory cortex asymmetry, altered minicolumn spacing and absence of ageing effects in schizophrenia. Brain, 131(12), 3178-3192.

Chance, S. A., Clover, L., Cousijn, H., Currah, L., Pettingill, R., & Esiri, M. M. (2011). Microanatomical correlates of cognitive ability and decline: normal ageing, MCI, and Alzheimer's disease. Cerebral Cortex, 21(8), 1870-1878.

Chance, S. A., Tzotzoli, P. M., Vitelli, A., Esiri, M. M., & Crow, T. J. (2004). The cytoarchitecture of sulcal folding in Heschl's sulcus and the temporal cortex in the normal brain and schizophrenia: lamina thickness and cell density. Neuroscience letters, 367(3), 384-388.

Cohen-Adad, J., Polimeni, J. R., Helmer, K. G., Benner, T., McNab, J. A., Wald, L. L., . . . & Mainero, C. (2012). T2* mapping and B0 orientation-dependence at 7 T reveal cyto- and myeloarchitecture organization of the human cortex. Neuroimage, 60(2), 1006-1014.

D'arceuil, H., & de Crespigny, A. (2007). The effects of brain tissue decomposition on diffusion tensor imaging and tractography. Neuroimage, 36(1), 64-68.

Di Rosa, E., Crow, T. J., Walker, M. A., Black, G., & Chance, S. A. (2009). Reduced neuron density, enlarged minicolumn spacing and altered ageing effects in fusiform cortex in schizophrenia. Psychiatry research, 166(2-3), 102-115.

Dumoulin, S. O., Fracasso, A., van der Zwaag, W., Siero, J. C., & Petridou, N. (2018). Ultra-high field MRI: advancing systems neuroscience towards mesoscopic human brain function. Neuroimage, 168, 345-357.

Fatterpekar, G. M., Naidich, T. P., Delman, B. N., Aguinaldo, J. G., Gultekin, S. H., Sherwood, C. C., . . . & Fayad, Z. A. (2002). Cytoarchitecture of the human cerebral cortex: MR microscopy of excised specimens at 9.4 Tesla. American journal of neuroradiology, 23(8), 1313-1321.

Fisher, E., Rudick, R. A., Simon, J. H., Cutter, G., Baier, M., Lee, J. C., . . . & Simonian, N. A. (2002). Eight-year follow-up study of brain atrophy in patients with M S. Neurology, 59(9), 1412-1420.

Harasty, J., Seldon, H. L., Chan, P., Halliday, G., & Harding, A. (2003). The left human speech-processing cortex is thinner but longer than the right. Laterality: Asymmetries of Body, Brain and Cognition, 8(3), 247-260.

Hasan, K. M., Sankar, A., Halphen, C., Kramer, L. A., Brandt, M. E., Juranek, J., . . . & Ewing-Cobbs, L. (2007). Development and organization of the human brain tissue compartments across the lifespan using diffusion tensor imaging. Neuroreport, 18(16), 1735-1739.

Heidemann, R. M., Anwander, A., Feiweier, T., Eichner, C., Lützkendorf, R., Bernarding, J., . . . & Turner, R. (2012). Sub-millimeter diffusion MRI at 7T: Does resolution matter?.

Heidemann, R. M., Anwander, A., Knösche, T. R., Feiweier, T., Fasano, F., Pfeuffer, J., & Turner, R. (2009). High Resolution Diffusion-Weighted Imaging Showing Radial Anisotropy in the Human Cortex In Vivo. In ISMRM Annual Meeting.

Huang, H., Jeon, T., Sedmak, G., Pletikos, M., Vasung, L., Xu, X., . . . & Mori, S. (2012). Coupling diffusion imaging with histological and gene expression analysis to examine the dynamics of cortical areas across the fetal period of human brain development. Cerebral cortex, 23(11), 2620-2631.

Jeon, T., Mishra, V., Uh, J., Weiner, M., Hatanpaa, K. J., White III, C. L., . . . & Huang, H. (2012). Regional changes of cortical mean diffusivities with aging after correction of partial volume effects. Neuroimage, 62(3), 1705-1716.

Jespersen, S. N., Leigland, L. A., Cornea, A., & Kroenke, C. D. (2012). Determination of axonal and dendritic orientation distributions within the developing cerebral cortex by diffusion tensor imaging. IEEE transactions on medical imaging, 31(1), 16-32.

Jones, S. E., Buchbinder, B. R., & Aharon, I. (2000). Three-dimensional mapping of cortical thickness using Laplace's Equation. Human brain mapping, 11(1), 12-32.

Kang, X., Herron, T. J., Turken, U., & Woods, D. L. (2012). Diffusion properties of cortical and pericortical tissue: regional variations, reliability and methodological issues. Magnetic Resonance Imaging, 30(8), 1111-1122.

Kim, T. H., Zollinger, L., Shi, X. F., Rose, J., & Jeong, E. K. (2009). Diffusion tensor imaging of ex vivo cervical spinal cord specimens: the immediate and long-term effects of fixation on diffusivity. The Anatomical Record: Advances in Integrative Anatomy and Evolutionary Biology: Advances in Integrative Anatomy and Evolutionary Biology, 292(2), 234-241.

Kleinnijenhuis, M., Zerbi, V., Küsters, B., Slump, C. H., Barth, M., & van Walsum, A. M. V. C. (2013). Layer-specific diffusion weighted imaging in human primary visual cortex in vitro. Cortex, 49(9), 2569-2582.

Kolasinski, J., Stagg, C. J., Chance, S. A., DeLuca, G. C., Esiri, M. M., Chang, E. H., . . . & Johansen-Berg, H. (2012). A combined post-mortem magnetic resonance imaging and quantitative histological study of multiple sclerosis pathology. Brain, 135(10), 2938-2951.

Kutzelnigg, A., & Lassmann, H. (2006). Cortical demyelination in multiple sclerosis: a substrate for cognitive deficits?. Journal of the neurological sciences, 245(1-2), 123-126.

Leuze, C. W., Dhital, B., Anwander, A., Pampel, A., Heidemann, R., Geyer, S., . . . & Turner, R. (2011). Visualization of the orientational structure of the human stria of Gennari with high-resolution DWI. In Proc Intl Soc Mag Reson Med (Vol. 19, p. 2371).

Leuze, C. W., Anwander, A., Bazin, P. L., Dhital, B., StOber, C., Reimann, K., . . . & Turner, R. (2012). Layer-specific intracortical connectivity revealed with diffusion MRI. Cerebral cortex, 24(2), 328-339.

McNab, J. A., Jbabdi, S., Deoni, S. C., Douaud, G., Behrens, T. E., & Miller, K. L. (2009). High resolution diffusion-weighted imaging in fixed human brain using diffusion-weighted steady state free precession. Neuroimage, 46(3), 775-785.

McNab, J. A., Polimeni, J. R., Wang, R., Augustinack, J. C., Fujimoto, K., Stevens, A., . . . & Wald, L. L. (2013). Surface based analysis of diffusion orientation for identifying architectonic domains in the in vivo human cortex. Neuroimage, 69, 87-100.

Miller, K. L., McNab, J. A., Jbabdi, S., & Douaud, G. (2012). Diffusion tractography of post-mortem human brains: optimization and comparison of spin echo and steady-state free precession techniques. Neuroimage, 59(3), 2284-2297.

Miller, K. L., Stagg, C. J., Douaud, G., Jbabdi, S., Smith, S. M., Behrens, T. E., . . . & Jenkinson, N. (2011). Diffusion imaging of whole, post-mortem human brains on a clinical MRI scanner. Neuroimage, 57(1), 167-181.

Mori, S., & Zhang, J. (2006). Principles of diffusion tensor imaging and its applications to basic neuroscience research. Neuron, 51(5), 527-539.

Mountcastle, V. B. (1997). The columnar organization of the neocortex. Brain: a journal of neurology, 120(4), 701-722.

Peters, A., Sethares, C., & Killiany, R. J. (2001). Effects of age on the thickness of myelin sheaths in monkey primary visual cortex. Journal of Comparative Neurology, 435(2), 241-248.

Preziosa P., Kiljan S., Steenwijk M. D., Meani A., van de Berg W. D. J., Schenk G. J., Rocca M. A., Filippi M., Geurts J. J. G., Jonkman L. E. (2019) Axonal degeneration as substrate of fractional anisotropy abnormalities in multiple sclerosis cortex. Brain. June 5. doi: 10.1093/brain/awz143. [Epub ahead of print]Quester, R., & Schröder, R. (1997). The shrinkage of the human brain stem during formalin fixation and embedding in paraffin. Journal of neuroscience methods, 75(1), 81-89.

Team, R. C. (2013). R: A language and environment for statistical computing.

Sarlls, J. E., & Pierpaoli, C. (2009). In vivo diffusion tensor imaging of the human optic chiasm at submillimeter resolution. Neuroimage, 47(4), 1244-1251.

Schmierer, K., Wheeler-Kingshott, C. A., Tozer, D. J., Boulby, P. A., Parkes, H. G., Yousry, T. A., . . . & Miller, D. H. (2008). Quantitative magnetic resonance of postmortem multiple sclerosis brain before and after fixation. Magnetic Resonance in Medicine: An Official Journal of the International Society for Magnetic Resonance in Medicine, 59(2), 268-277.

Seldon, H. L. (1981). Structure of human auditory cortex. II. Axon distributions and morphological correlates of speech perception. Brain Research, 229(2), 295-310.

Setsompop, K., Fan, Q., Stockmann, J., Bilgic, B., Huang, S., Cauley, S. F., . . . & Wald, L. L. (2018). High-resolution in vivo diffusion imaging of the human brain with generalized slice dithered enhanced resolution: Simultaneous multislice (g S lider—SMS). Magnetic resonance in medicine, 79(1), 141-151.

Shepherd T M, Thelwall P E, Stanisz G J, Blackband S J. (2009) Aldehyde fixative solutions alter the water relaxation and diffusion properties of nervous tissue. Magn Reson Med. 62(1):26-34. doi: 10.1002/mrm.21977.

Sigalovsky, I. S., Fischl, B., & Melcher, J. R. (2006). Mapping an intrinsic MR property of gray matter in auditory cortex of living humans: a possible marker for primary cortex and hemispheric differences. Neuroimage, 32(4), 1524-1537.

Smith, S. M., Jenkinson, M., Woolrich, M. W., Beckmann, C. F., Behrens, T. E., Johansen-Berg, H., . . . & Niazy, R. K. (2004). Advances in functional and structural M R image analysis and implementation as FSL. Neuroimage, 23, S208-S219.

Song S K, Sun S W, Ramsbottom M J, Chang C, Russell J, Cross A H. (2002) Dysmyelination revealed through MRI as increased radial (but unchanged axial) diffusion of water. Neuroimage, 17(3):1429-36.

Sotiropoulos S. N., Jbabdi S., Xu J., Andersson J. L., Moeller S., Auerbach E. J., Glasser M. F., Hernandez M., Sapiro G., Jenkinson M., Feinberg D. A., Yacoub E., Lenglet C., Van Essen D. C., Ugurbil K., Behrens T. E.; W U-Minn HCP Consortium. (2013). Advances in diffusion MRI acquisition and processing in the Human Connectome Project. Neuroimage, 80, 125-143.

Tommerdahl, M., Tannan, V., Holden, J. K., & Baranek, G. T. (2008). Absence of stimulus-driven synchronization effects on sensory perception in autism: Evidence for local underconnectivity?. Behavioral and Brain Functions, 4(1), 19.

Uğurbil, K., Xu, J., Auerbach, E. J., Moeller, S., Vu, A. T., Duarte-Carvajalino, J. M., . . . & Strupp, J. (2013). Pushing spatial and temporal resolution for functional and diffusion MRI in the Human Connectome Project. Neuroimage, 80, 80-104.

van Veluw, S. J., Sawyer, E. K., Clover, L., Cousijn, H., De Jager, C., Esiri, M. M., & Chance, S. A. (2012). Prefrontal cortex cytoarchitecture in normal aging and Alzheimer's disease: a relationship with IQ. Brain structure and function, 217(4), 797-808.

von Economo, C. F., & Koskinas, G. N. (1925). Die cytoarchitektonik der hirnrinde des erwachsenen menschen. J. Springer.

Vrenken, H., Pouwels, P. J., Geurts, J. J., Knol, D. L., Polman, C. H., Barkhof, F., & Castelijns, J. A. (2006). Altered diffusion tensor in multiple sclerosis normal-appearing brain tissue: cortical diffusion changes seem related to clinical deterioration. Journal of Magnetic Resonance Imaging: An Official Journal of the International Society for Magnetic Resonance in Medicine, 23(5), 628-636.

Wegner, C., Esiri, M. M., Chance, S. A., Palace, J., & Matthews, P. M. (2006). Neocortical neuronal, synaptic, and glial loss in multiple sclerosis. Neurology, 67(6), 960-967.

Woolrich, M. W., Jbabdi, S., Patenaude, B., Chappell, M., Makni, S., Behrens, T., . . . & Smith, S. M. (2009). Bayesian analysis of neuroimaging data in FSL. Neuroimage, 45(1), S173-S186.

The invention claimed is:

1. A computer-implemented method for determining an indication of a level of a cognitive disorder in a subject, or an indication of a number of microsegment breaks in a region of a subject's brain, the computer-implemented method comprising:

obtaining, at a magnetic resonance imaging device, at least one magnetic resonance image of the subject's brain;

receiving, at a computing device, diffusion data obtained from the at least one magnetic resonance image of the subject's brain;

pre-processing the diffusion data;

determining, from the pre-processed diffusion data, a principal diffusion direction in at least one first voxel in a region of grey matter in the subject's brain;

determining, from the pre-processed diffusion data, an average columnar direction of minicolumns in the at least one first voxel;

determining, from the pre-processed diffusion data, a value for an angle of deviation (AngleR) between the principal diffusion direction and the average columnar direction of minicolumns in the at least one first voxel;

determining, from the pre-processed diffusion data, a value for Axial Diffusivity in at least one second voxel in a region of white matter associated with underlying the region of grey matter;

determining a value for Axial Columnar Refraction (ACR) for each of the at least one first voxel and the at least one second voxel using the values for AngleR and Axial Diffusivity;

comparing the values of ACR with corresponding reference measurements derived from pre-obtained reference data; and determining, based on the comparison, the indication of the level of a cognitive disorder in the subject, or the indication of the number of microsegment breaks in the region of the subject's brain.

2. The computer-implemented method as claimed in claim 1, wherein the magnitude of the values of ACR for the at least one first voxel and the at least one second voxel in comparison to the corresponding reference measurements provides an indication of the level of a cognitive disorder in the subject.

3. The computer-implemented method as claimed in claim 1, wherein the magnitude of the values of ACR for the at least one first voxels and the at least one second voxels provides an indication of the number of microsegment breaks in the region.

4. The computer-implemented method as claimed in claim 1, wherein the value for AngleR and/or Axial Diffusivity is obtained from or derived from one or more regions of the cortex of the brain.

5. The computer-implemented method as claimed in claim 4, wherein the region of the brain is selected from the group consisting of parahippocampal gyrus (PHG), fusiform gyrus (Fusi), dorsolateral prefrontal cortex area 9 (dlPFC), area 41, Heschl's gyrus (HG), planum temporale (PT), inferior parietal lobule (IPL), middle temporal gyrus (MTG), primary visual cortex (V1; area 17) and entorhinal cortex.

6. The computer-implemented method as claimed in claim 1, wherein the subject is one who has a cognitive disorder selected from the group consisting of Alzheimer's Disease (AD), cerebrovascular dementia (CVD), mild cognitive impairment (MCI), frontotemporal dementia (FTD), dementia with Lewy Bodies (DLB), autism, multiple sclerosis (MS), epilepsy, amyotrophic lateral sclerosis (ALS), Parkinson's disease, schizophrenia, bipolar disorder, dyslexia, Down's syndrome, Huntington's disease, prion disease, depression, obsessive-compulsive disorder or attention deficit hyperactivity disorder (ADHD), Subjective Cognitive Impairment, preMCI, and prodromal AD, Posterior Cortical Atrophy (subset of AD), behavioural, semantic, or progressive non-fluent aphasia (subsets of FTD), encephalopathy, hepatic encephalopathy, stroke, ischaemia, ischaemic hypoxia, neuro-inflammation, traumatic brain injury (TBI), mild TBI, chronic traumatic encephalopathy, concussion and delirium.

7. A method of treatment of a subject, wherein the method comprises the computer-implemented method as claimed in claim 1, wherein, if the subject is found have a level of a cognitive disorder beyond (above or below) a specified reference level or is found to have a value for ACR above a specified reference level, a cognitive-disorder treating medicament is administered to the subject.

8. A method of treatment of a subject, wherein the method comprises obtaining or receiving results of the computer-implemented method for determining ACR as claimed in claim 1, and if the ACR value is higher than a reference level, thereby providing an indication of the presence of a cognitive disorder in the subject, administering a treatment to the subject appropriate for treating the cognitive disorder.

9. A system or apparatus comprising at least one processing means arranged to carry out the steps of the computer-implemented method as claimed in claim 1.

10. A non-transitory carrier bearing software comprising instructions for configuring a processor to carry out the steps of the computer-implemented method as claimed in claim 1.

11. A system for determining an indication of a level of a cognitive disorder in a subject, the system comprising:

a magnetic resonance imaging device configured to acquire diffusion data; and processing means configured to:
  pre-process the diffusion data;
  determine, from the pre-processed diffusion data, a principal diffusion direction in at least one first voxel in a region of grey matter in the subject's brain;
  determine, from the pre-processed diffusion data, an average columnar direction of minicolumns in the at least one first voxel;
  determine, from the pre-processed diffusion data, a value for an angle of deviation (AngleR) between the principal diffusion direction and the average columnar direction of minicolumns in the at least one first voxel;
  determine, from the pre-processed diffusion data, a value for Axial Diffusivity in at least one second voxel in a region of white matter associated with underlying the region of grey matter;
  determine a value for Axial Columnar Refraction (ACR) for each of the at least one first voxel and the at least one second voxel using the values for AngleR and Axial Diffusivity;
  compare the values of ACR with corresponding reference measurements derived from pre-obtained reference data; and
  determine, based on the comparison, the indication of the level of a cognitive disorder in the subject.

\* \* \* \* \*